(12) United States Patent
Holmes et al.

(10) Patent No.: US 12,209,290 B2
(45) Date of Patent: *Jan. 28, 2025

(54) SYSTEMS AND METHODS FOR ANALYTE TESTING AND LABORATORY OVERSIGHT

(71) Applicant: Labrador Diagnostics LLC, Healdsburg, CA (US)

(72) Inventors: Elizabeth A. Holmes, Palo Alto, CA (US); Timothy Smith, San Ramon, CA (US); Samartha Anekal, San Jose, CA (US); James R. Wasson, Los Altos, CA (US); Daniel L. Young, San Francisco, CA (US); Chinmay Pangarkar, Fremont, CA (US)

(73) Assignee: Labrador Diagnostics LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 17/319,906

(22) Filed: May 13, 2021

(65) Prior Publication Data

US 2021/0404022 A1    Dec. 30, 2021

Related U.S. Application Data

(63) Continuation of application No. 14/490,653, filed on Sep. 18, 2014, now Pat. No. 11,008,628, which is a continuation-in-part of application No. 14/183,500, filed on Feb. 18, 2014, now Pat. No. 9,810,704.

(60) Provisional application No. 61/882,624, filed on Sep. 25, 2013, provisional application No. 61/879,671, filed on Sep. 18, 2013, provisional application No. 61/766,119, filed on Feb. 18, 2013, provisional application No. 61/766,113, filed on Feb. 18, 2013.

(51) Int. Cl.
| | |
|---|---|
| B01L 3/00 | (2006.01) |
| B01L 7/00 | (2006.01) |
| C12Q 1/70 | (2006.01) |
| G01N 33/569 | (2006.01) |

(52) U.S. Cl.
CPC ............... *C12Q 1/70* (2013.01); *B01L 3/52* (2013.01); *B01L 7/52* (2013.01); *G01N 33/56983* (2013.01); *B01L 2400/043* (2013.01); *G01N 2333/11* (2013.01); *G01N 2469/20* (2013.01)

(58) Field of Classification Search
CPC ......... G01N 33/56983; G01N 2333/11; G01N 2469/20; B01L 3/52; B01L 7/52; B01L 2400/043; C12Q 1/70

See application file for complete search history.

(56) References Cited

U.S. PATENT DOCUMENTS

| | | |
|---|---|---|
| 5,358,691 A | 10/1994 | Clark et al. |
| 5,647,994 A | 7/1997 | Tuunanen et al. |
| 6,060,022 A | 5/2000 | Pang et al. |
| 6,551,784 B2 | 4/2003 | Fodor et al. |
| 8,380,541 B1 | 2/2013 | Holmes |

(Continued)

OTHER PUBLICATIONS

Notice of Allowance dated Oct. 26, 2016 for U.S. Appl. No. 14/490,658.

(Continued)

*Primary Examiner* — Jill A Warden
*Assistant Examiner* — Michael Stanley Gzybowski
(74) *Attorney, Agent, or Firm* — Sterne, Kessler, Goldstein & Fox P.L.L.C.

(57) ABSTRACT

In one embodiment, a method is provided comprising analyte testing on one or more types of samples.

13 Claims, 10 Drawing Sheets

(56) References Cited

U.S. PATENT DOCUMENTS

| | | |
|---|---|---|
| 8,899,118 B1 | 12/2014 | Seguin |
| 9,168,523 B2 | 10/2015 | Ludowise et al. |
| 10,401,373 B1 | 9/2019 | Holmes et al. |
| 11,008,628 B1 | 5/2021 | Holmes et al. |
| 2001/0019845 A1 | 9/2001 | Bienert et al. |
| 2002/0059030 A1 | 5/2002 | Otworth et al. |
| 2002/0065457 A1 | 5/2002 | Kuth |
| 2002/0074882 A1 | 6/2002 | Werfel et al. |
| 2002/0085952 A1 | 7/2002 | Ellingboe et al. |
| 2002/0108857 A1 | 8/2002 | Paschetto et al. |
| 2002/0120187 A1 | 8/2002 | Eiffert et al. |
| 2002/0141904 A1 | 10/2002 | Rosen et al. |
| 2002/0144458 A1 | 10/2002 | Hunter et al. |
| 2002/0149772 A1 | 10/2002 | Halg |
| 2002/0155599 A1 | 10/2002 | Vellinger et al. |
| 2002/0155616 A1 | 10/2002 | Hiramatsu et al. |
| 2002/0160353 A1 | 10/2002 | Sundaram et al. |
| 2002/0161606 A1 | 10/2002 | Bennett et al. |
| 2002/0164770 A1 | 11/2002 | Hoffmann |
| 2003/0012699 A1 | 1/2003 | Moore et al. |
| 2003/0100822 A1 | 5/2003 | Lew et al. |
| 2003/0127609 A1 | 7/2003 | El-Hage et al. |
| 2003/0138140 A1 | 7/2003 | Marcelpoil et al. |
| 2004/0020310 A1 | 2/2004 | Escal |
| 2004/0022677 A1 | 2/2004 | Wohlstadter et al. |
| 2004/0029266 A1 | 2/2004 | Barbera-Guillem |
| 2004/0055361 A1 | 3/2004 | Schneider et al. |
| 2004/0086872 A1 | 5/2004 | Childers et al. |
| 2004/0087426 A1 | 5/2004 | Lattanzi |
| 2004/0115720 A1 | 6/2004 | McWilliams et al. |
| 2004/0134750 A1 | 7/2004 | Luoma, II |
| 2004/0161368 A1 | 8/2004 | Holtlund et al. |
| 2004/0166027 A1 | 8/2004 | Wilmer et al. |
| 2004/0209266 A1 | 10/2004 | Squirrell |
| 2004/0241043 A1 | 12/2004 | Sattler |
| 2004/0241048 A1 | 12/2004 | Shin et al. |
| 2005/0100937 A1 | 5/2005 | Holmes |
| 2005/0147559 A1 | 7/2005 | von Alten |
| 2005/0152900 A1 | 7/2005 | Najib et al. |
| 2005/0164204 A1 | 7/2005 | Reed |
| 2005/0220668 A1 | 10/2005 | Coville |
| 2005/0225751 A1 | 10/2005 | Sandell et al. |
| 2005/0231723 A1 | 10/2005 | Blasenheim et al. |
| 2005/0236317 A1 | 10/2005 | DeSilets et al. |
| 2006/0013733 A1 | 1/2006 | Meeks et al. |
| 2006/0019274 A1 | 1/2006 | Goel |
| 2006/0024841 A1 | 2/2006 | Yao et al. |
| 2006/0057599 A1 | 3/2006 | Dzenitis et al. |
| 2006/0062852 A1 | 3/2006 | Holmes |
| 2006/0073538 A1 | 4/2006 | Konrad |
| 2006/0074063 A1 | 4/2006 | Fernandez-Pol |
| 2006/0083660 A1 | 4/2006 | Schorno et al. |
| 2006/0110725 A1 | 5/2006 | Lee et al. |
| 2006/0115384 A1 | 6/2006 | Wohleb |
| 2006/0121502 A1 | 6/2006 | Cain et al. |
| 2006/0264783 A1 | 11/2006 | Holmes et al. |
| 2007/0125677 A1 | 6/2007 | Oronsky et al. |
| 2007/0172100 A1 | 7/2007 | Lefebvre |
| 2007/0207450 A1 | 9/2007 | Rodgers et al. |
| 2009/0088336 A1 | 4/2009 | Burd et al. |
| 2009/0117620 A1 | 5/2009 | Fritchie et al. |
| 2009/0221059 A1 | 9/2009 | Williams et al. |
| 2010/0126286 A1 | 5/2010 | Self et al. |
| 2010/0180980 A1 | 7/2010 | Lee et al. |
| 2010/0216657 A1 | 8/2010 | Hukari et al. |
| 2011/0007261 A1 | 1/2011 | Abbott et al. |
| 2012/0178091 A1 | 7/2012 | Glezer et al. |
| 2012/0309104 A1 | 12/2012 | Uematsu et al. |
| 2012/0309636 A1 | 12/2012 | Gibbons et al. |
| 2014/0087370 A1 | 3/2014 | Maeshima |
| 2015/0239130 A1 | 8/2015 | Buchloh et al. |
| 2016/0025760 A1 | 1/2016 | Holmes |
| 2020/0081023 A1 | 3/2020 | Holmes et al. |

OTHER PUBLICATIONS

Office Action dated Nov. 16, 2017 for U.S. Appl. No. 14/631,830.
Office Action dated Dec. 29, 2017 for U.S. Appl. No. 15/584,374.
Office Action dated Feb. 24, 2016 for U.S. Appl. No. 14/631,830.
Office Action dated Apr. 14, 2016 for U.S. Appl. No. 14/490,658.
Office Action dated Jul. 30, 2018 for U.S. Appl. No. 14/631,830.
Office Action dated Jul. 8, 2015 for U.S. Appl. No. 14/490,658.
Office Action dated Sep. 6, 2016 for U.S. Appl. No. 14/631,830.

SYSTEMS AND METHODS FOR ANALYTE TESTING AND LABORATORY OVERSIGHT

BACKGROUND

Laboratory testing of blood samples from patients has traditionally been based on venipuncture performed at a laboratory facility or a patient service center. Typically, after waiting for their turn at that facility or center, a patient is then attended to by a phlebotomist who extracts blood from the patient. Before venipuncture, the phlebotomist selects the correct number and type of vacuum blood collection tubes for the desired number and/or types of tests set forth in the laboratory test request. The phlebotomist ensures that blood from the venipunture fills the correct number and types of tubes. Unless the laboratory tests were ordered STAT or other expedited basis, the patient will wait days or weeks before being notified of the results of the laboratory test. Usually, the notification comes from the doctor or someone in the doctor's office, not from the laboratory that conducted the test.

This process of traditional testing protocol and traditional testing infrastructure, creates a legacy system that can be unnecessarily slow and burdened by various limitations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

SUMMARY

The disadvantages associated with the prior art are overcome by at least some of the embodiments of systems and methods provided herein.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DESCRIPTION OF THE SPECIFIC EMBODIMENTS

Figure 1:
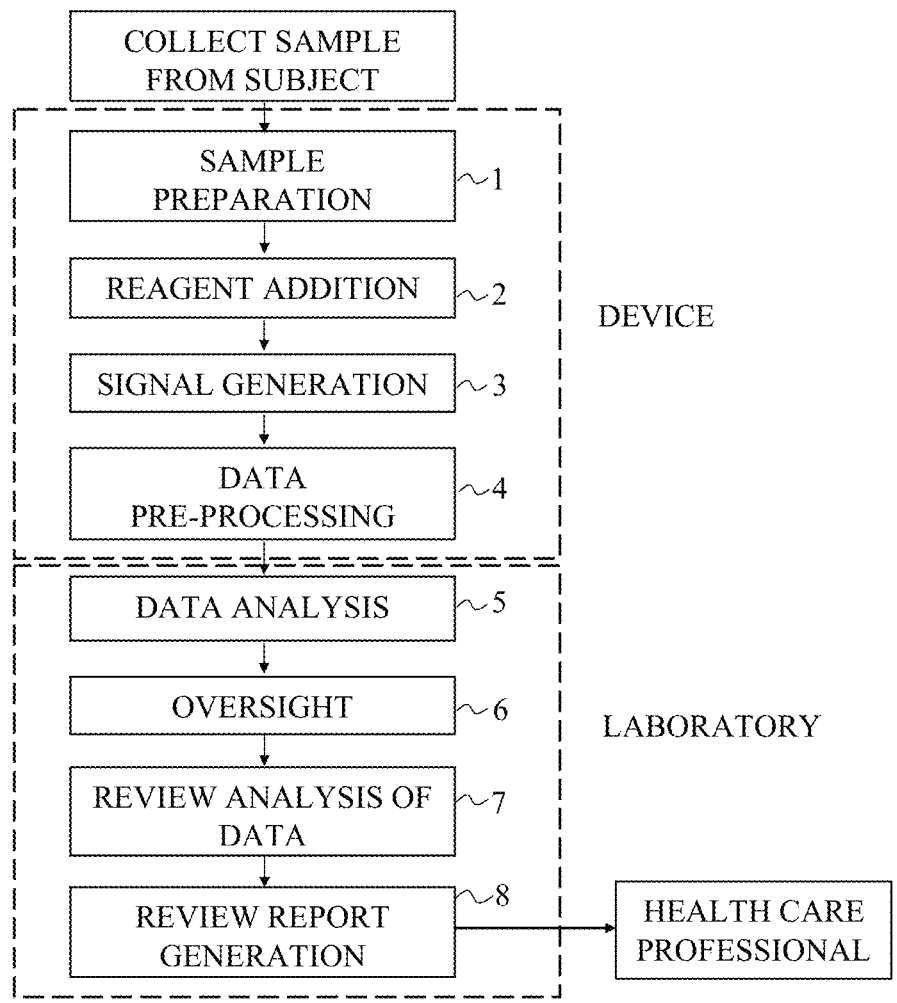
FIG. 1 shows a schematic of one embodiment of a system as described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Referring now to FIG. 1, according to a least one embodiment herein, a system is provided that is a Clinical Laboratory Improvement Amendments ("CLIA")-certified laboratory's automated sample processing and analysis system (the "System") comprising Sample Processing Units ("SPUs"), a Laboratory Automation System ("LAS"), and assays, which in one non-limiting example includes influenza NAA and ELISA assays. In one non-limiting example, the assays may be physically embodied in part as a cartridge, frame, pouch, or other physical holder that has one or more reagents and/or other materials (vessels, pipette tips, etc. . . . ) for use in processing samples on the SPU for these assays.

In at least one embodiment described herein, SPUs provide automated, pre-analytic sample processing for the purpose of substantially reducing human error in sample preparation, extraction, and processing, and for reducing the associated variability and error in test results.

The SPU and LAS were designed to automate the exact processing steps and protocols associated with the most precise and accurate CLIA-certified test methods. In one non-limiting example, SPUs will not be sold, but instead used only by in Patient Service Centers ("PSCs"), under the control and oversight of the CLIA-certified laboratory, for the purpose of providing the highest integrity clinical laboratory services. In such an example, the laboratory services are sold, but not the hardware. Optionally, some embodiments may sell, for example, the hardware, the disposables, the services, and/or single or multiple combinations of the foregoing.

In one embodiment, the development of the SPU and LAS is to provide a certified laboratory infrastructure where a high level of oversight could be combined with rapid processing of fresh samples by automation of the pre-analytic testing process in field, while maintaining all the performance, validated protocols, and infrastructure associated with processing and running tests in a CLIA-certified laboratory.

In one non-limiting example, this comprises leveraging the use of secure server software to control medical devices and enable two-way communication to and from medical devices, wherein automation of pre-analytic processing steps with CLIA-certified laboratory oversight at PSCs increases the quality of patient care by enabling a faster generation of lab results for physicians, minimizing errors associated with pre-analytic and human processing, the largest contributor of error in laboratory testing, enabling processing of fresh samples to minimize the impact of analyte decay rates and the associated clinical relevance of results reported back to clinicians, minimizing the impact of sample shipments, temperature, environment, and human-related variability on result variability and sample chain-of-custody issues, facilitating micro-sample testing for better patient experience and compliance, and providing oversight of processing steps that have the potential to cause test variability or error.

In this non-limiting example, signals generated by the SPU during pre-analytic processing are transmitted to the CLIA-certified laboratory (or optionally, another laboratory certified for clinical testing), which will then conduct the analytic and post-analytic steps of the testing process through the LAS, which can process the signals received from the SPU into test results and review replicate data, outliers, controls, and/or calibrator values in doing so. Such data, outliers, controls, and/or calibrator values are of those from at least one SPU in the field. After analyzing the data through the LAS, the CLIA-certified laboratory will generate a test report, which will be transmitted to the health care professional that ordered a given test.

As referenced above, the laboratory leverages customized secure network connectivity to connect with SPUs, making it possible for those SPUs to be placed in The CLIA-certified laboratory's Patient Service Centers or sample collection sites, while constantly remaining under the control of the LAS overseen by CLIA-certified central laboratory.

Furthermore for at least one embodiment herein, the LAS provides control and secure two-way communication with the SPUs to enable CLIA-compliant oversight of sample processing devices, while being placed at the locations in which the sample processing can be done with the minimum number of errors associated with transportation and human handling. The secure information and control communicated between the SPU and LAS allows for oversight to be extended from the central LAS to the remote SPU. In this manner, the SPU remains a core component of The CLIA-certified laboratory and a core part of realizing the quality standards of The CLIA-certified laboratory. The combination of reducing human error from pre-analytic processing while maintaining CLIA-compliant oversight and control of the devices provides for higher quality results and repeatable test procedures.

This non-limiting description describes the use of the SPU and LAS in reporting nucleic acid-based and enzyme-linked immunosorbent assay ("ELISA")-based Influenza test results. The SPU is capable of automated extraction and processing of nucleic acids from multiple sample types, as well as the automated amplification of target nucleic acid sequences by fluorescence-based nucleic acid amplification that generates signals transported to the LAS for analysis. In one non-limiting example, the same SPU is also capable of automated preparation and processing of samples for use in ELISA-based protocols, again generating signals sent to the LAS for analysis.

Referring to FIG. 1, one embodiment of a system is now described. An outline of the system is shown in schematic in FIG. 1 depicting the pre-analytical (such as but not limited to sample processing, performed by the SPU as controlled by the LAS), analytical (such as but not limited to report generation, performed by the LAS), and post-analytical (such as but not limited to report transmission, performed by the LAS) parts. This may be indicated in part by the phantom rectangles shown in FIG. 1 to denote groupings of certain processes.

In one embodiment, the system described in this document comprises of the following components operating under oversight of The CLIA-certified laboratory: The Sample Processing Unit ("SPU"), designed to be housed in a Patient Service Center ("PSC"), and a centralized Laboratory Automation System ("LAS"), which is overseen by the CLIA-certified laboratory, running Influenza assays through nucleic assay amplification and ELISA-based protocols.

In one non-limiting example, the primary applications of the nucleic acid amplification and ELISA assays are to (i) accurately detect the presence of influenza virus subtypes (Influenza A, Influenza A subtype H1, Influenza A subtype 2009 H1, Influenza A subtype H3, Influenza A subtype H5N1, Influenza A subtype H7N9, and/or Influenza B) and (ii) to measure the corresponding serum antibody response by quantifying the concentration of influenza A and influenza B antibodies. Optionally, the system may be configured to detect the presence of at least two of the influenza virus subtypes (Influenza A, Influenza A subtype H1, Influenza A subtype 2009 H1, Influenza A subtype H3, Influenza A subtype H5N1, Influenza A subtype H7N9, Influenza B)) and (ii) to measure the corresponding serum antibody response by quantifying the concentration of influenza A and influenza B antibodies.

In this non-limiting example, the presence of influenza viral subtypes is determined through a nucleic acid amplification assay (Nucleic Acid Amplification assay, ("NAA") assay), and the antibody response is measured via an immunoassay.

Sample for the NAA assay may be collected in the form of a nasopharyngeal swab, nasopharyngeal aspirate, nasopharyngeal wash, and/or nasal swab. Sample for the immunoassay may be whole blood collected by a fingerstick, venipuncture, or a small volume, sub 500 uL blood collection from another location on the subject.

In one non-limiting example, the swab and whole blood samples are collected and introduced into a disposable Cartridge at a PSC and fed to the SPU, where the samples undergo processing and reaction steps, and are eventually introduced to a detector to yield a set of signals. These signal sets are transferred to the LAS where the raw data is processed and analyzed and oversight of the laboratory including SPU(s) is provided, and the relevant reportables are generated.

FIG. 1 shows a schematic diagram of the workflow of one embodiment of the system. Steps illustrated by boxes numbered from 1 to 4 represent pre-analytic steps. Pre-analytic steps include sample collection, sample processing, reagent addition, signal generation, and transmission. Steps illustrated by boxes numbered from 5 to 8 represent analytic steps. Analytic steps include analysis of data received from a device at a sample collection site, oversight, including analysis of controls, calibrations, replicates, outliers, device and sample identification and quality information, and generation of the reportable. Transmission of the report to the health care professional represents a post-analytic step. Post-analytic steps include further review of the analysis of data, and review of report generation and of the report generated for a particular test prior to sign off by CLIA-laboratory personnel and transmission to the physician who ordered a given test.

Figure 2:
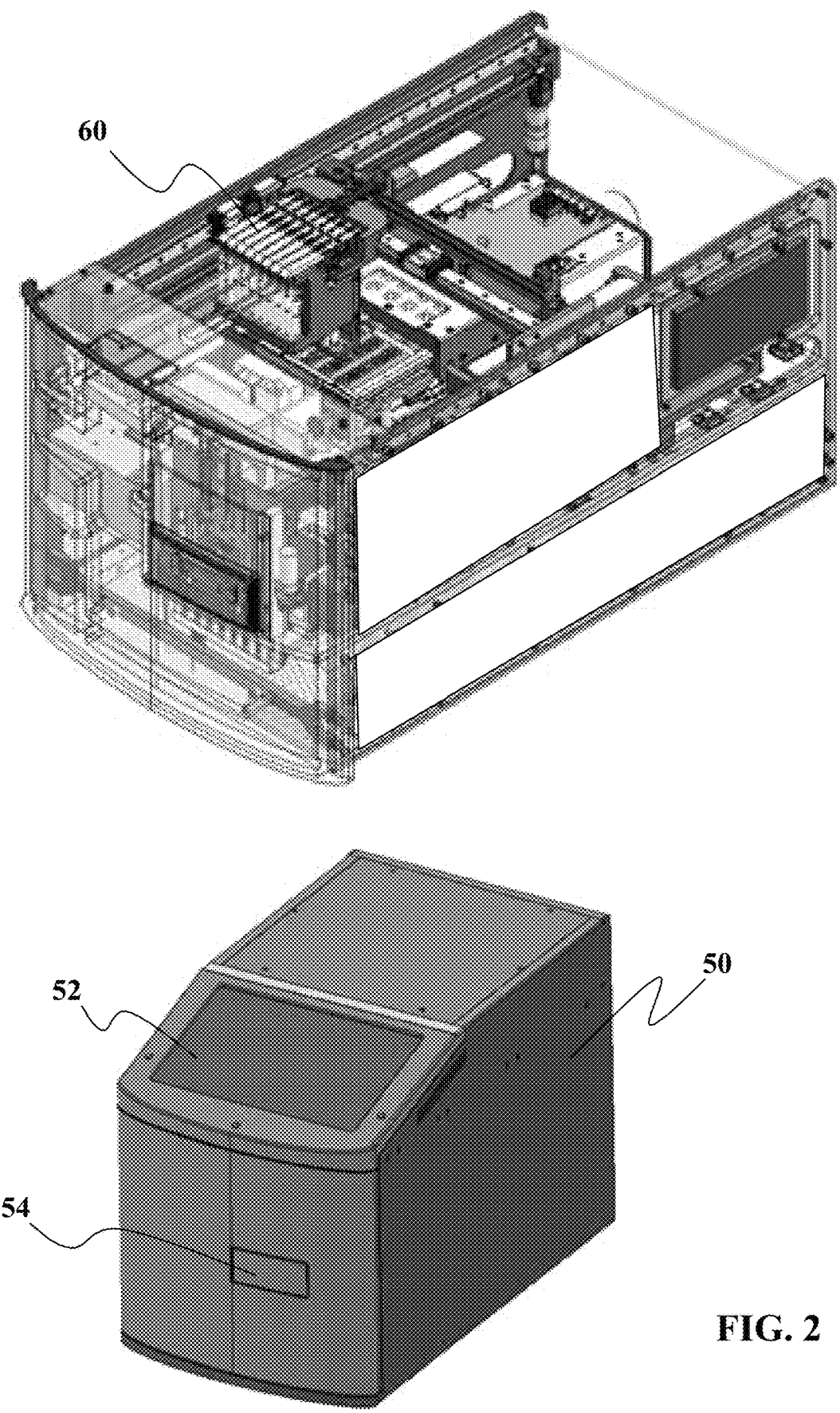
FIG. 2 show perspective views of one embodiment of a system as described herein.

Referring now to FIG. 2, one embodiment of a Sample Processing Unit (SPU) is shown: (L) without enclosure and (R) with enclosure. It should be understood that the modules herein may be included in configurations as shown or as described in U.S. Patent Application Ser. No. 61/769,119 fully incorporated herein by reference for all purposes. In one embodiment, the SPU contains no more than two types of the modules listed in the module list below. Optionally, the SPU contains no more than three types of the modules listed. Optionally, the SPU contains no more than four types of the modules listed. Optionally, the SPU contains no more than five types of the modules listed. Optionally, the SPU contains no more than six types of the modules listed. Optionally, the SPU contains no more than seven types of the modules listed. Optionally, the SPU contains no more than eight types of the modules listed. Optionally, the SPU contains no more than nine modules of the items listed. Optionally, the SPU contains no more than ten types of the modules listed. Optionally, the SPU contains no more than eleven types of the modules listed.

In this non-limiting example, the SPU is a modular hardware unit (FIG. 2) utilized for performing the pre-analytic functions described in the "Device Description—The System" Section. The SPU was designed to automatically replicate the processing systems used in the relevant traditional 'gold-standard' assay protocols. In this example, the SPU is enclosed in a thermally insulated and light-tight sheet metal enclosure 50. Optionally, other light tight materials may be used with or in place of metal. A user interface may be shown on the display 52. Optionally, display 52 is a touch screen display. FIG. 1 also shows a cartridge insertion door 54 that may be located along one surface of the enclosure 50. In one non-limiting example, the SPU comprises of the following components:

1. Liquid Handling Module 60
2. Centrifuge Module 70
3. Sonicator Module 80
4. Magnet Tool 90
5. Detector 1—Luminometer Module 100
6. Detector 2—Fluorometer Module 110
7. Detector 3—Fluorometer/Turbidimeter Module 120
8. Detector 4—Spectrophotometer Module 130
9. Detector 5—Microscopy Module 140
10. Thermal Control System
11. Machine Vision System and Materials It should be understood that this non-limiting description covers nucleic acid amplification ("NAA") and enzyme-linked immunosorbent ("ELISA") assays. Optionally, other assays based on other detection techniques can also be in multiplex fashion on the device.

For at least one embodiment herein, Modules 1-5, 7, the Thermal Control System (10), and the Machine Vision System (11) are used in connection with the NAA and ELISA assays.

Modules 6, 7, and 9 have been included here and briefly described for completeness. These modules are not used for NAA or ELISA assays.

Optionally, the SPU is composed of both purchased components, machined parts, and molded parts. Most of the machined parts are made of aluminum, with stainless steel used in parts where greater tensile strength is required.

1. Liquid Handling Module

Figure 3:
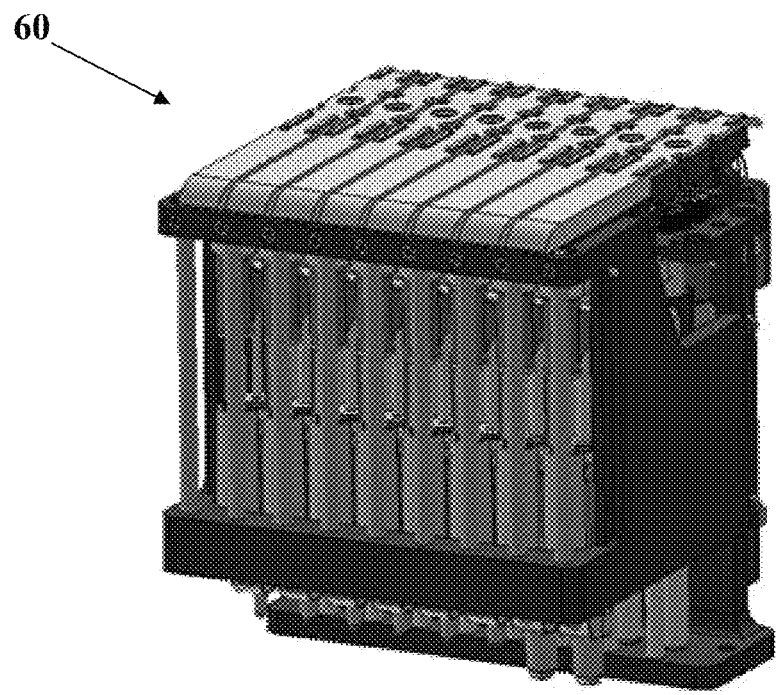
FIG. 3 shows a perspective view of one embodiment of a sample handling apparatus as described herein.

Referring now to FIG. 3, one non-limiting example of an automated liquid handling and processing module 60 (FIG. 3) is an electromechanical pipette-based assembly that resides within the SPU. The pipette assembly is mounted onto a controllable gantry. This gantry moves the pipette assembly horizontally throughout the SPU, allowing it to access different modules. The pipette assembly has individual pipette cards, each of which is independently actuated in the vertical direction. Each pipette card is capable of individually aspirating and dispensing fluids (including samples and reagents). The pipette assembly is used for engaging with vessels, for moving and mixing sample using pipette tips and vessels, and for moving those tips and vessels within the SPU. One pipette card in the Liquid Handling Module is configured to actuate the Magnetic Tool for sample processing, including extraction and purification as described in the "Device Description—Sample Processing Unit (SPU) and Materials—4. Magnet Tool" Section.

2. Centrifuge Module

Figure 4:
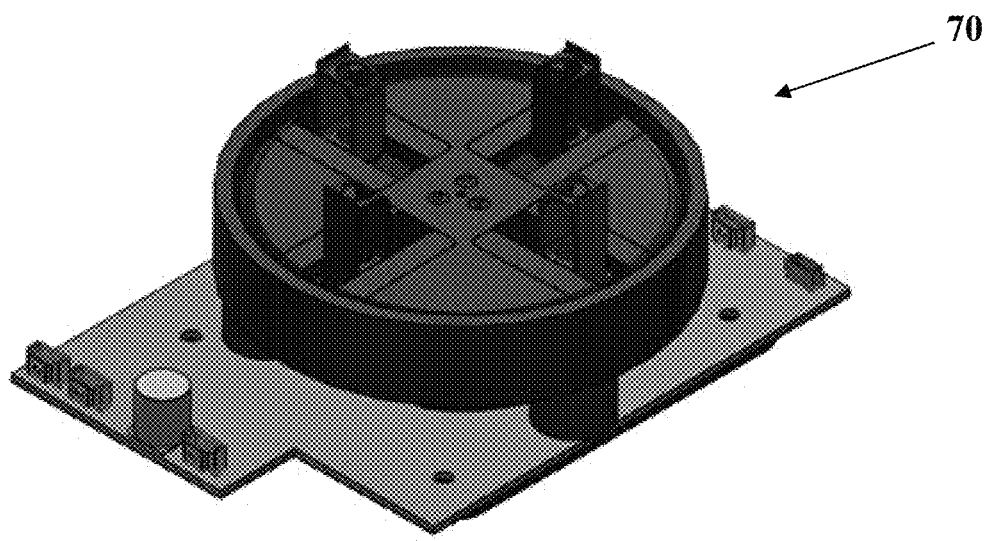
FIG. 4 shows a perspective view of one embodiment of a sample separation apparatus as described herein.

Referring now to FIG. 4, one non-limiting example of an on-board centrifuge 70 (FIG. 4) is a horizontal centrifuge used for separations in the SPU. The centrifuge can hold 4 centrifuge tubes, is powered by a DC motor with an optical encoder, and is capable of achieving speeds of up to 10,000 RPM (and thus providing up to 3300 g of centrifugal acceleration).

3. Sonicator Module

Figure 5:
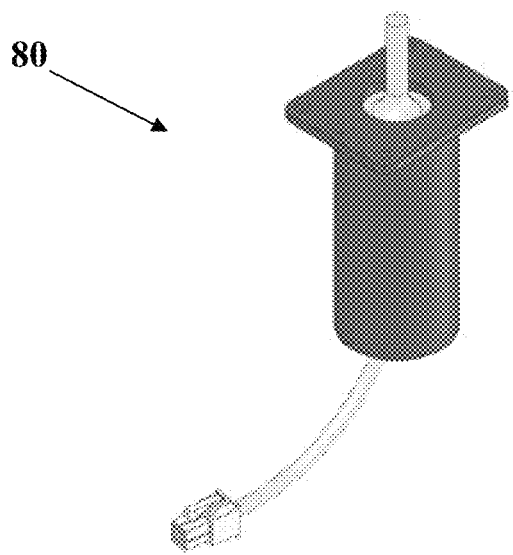
FIG. 5 shows a perspective view of one embodiment of a sample sonication apparatus as described herein.

Referring now to FIG. 5, one non-limiting example of a sonicator 80 (FIG. 5) is used during sample preparation steps to lyse cells, freeing the DNA for further processing and data generation. In one nonlimiting example, the sonicator assembly comprises of a commercially available 40 kHz sonotrode, housing, and power supply electronics. Optionally, other embodiments may use a sonotrode designed for a different frequency. During sample purification, the sample is placed in a polystyrene vessel. This vessel is moved to the sonicator, using the automated liquid handling system. The handling system establishes contact between the vessel and sonicator by pushing the vessel against the sonicator probe with a slight amount of force. Once contact has been firmly established, the sonicator is energized. This transmits mechanical energy into the vessel and sample, causing cavitation and eventual lysis within the sample. Sonication energy can be modulated in power and applied in a continuous or pulsed fashion. Once sonication is complete, the liquid handling system returns the sample vessel for further purification processing.

4. Magnet Tool

Figure 6:
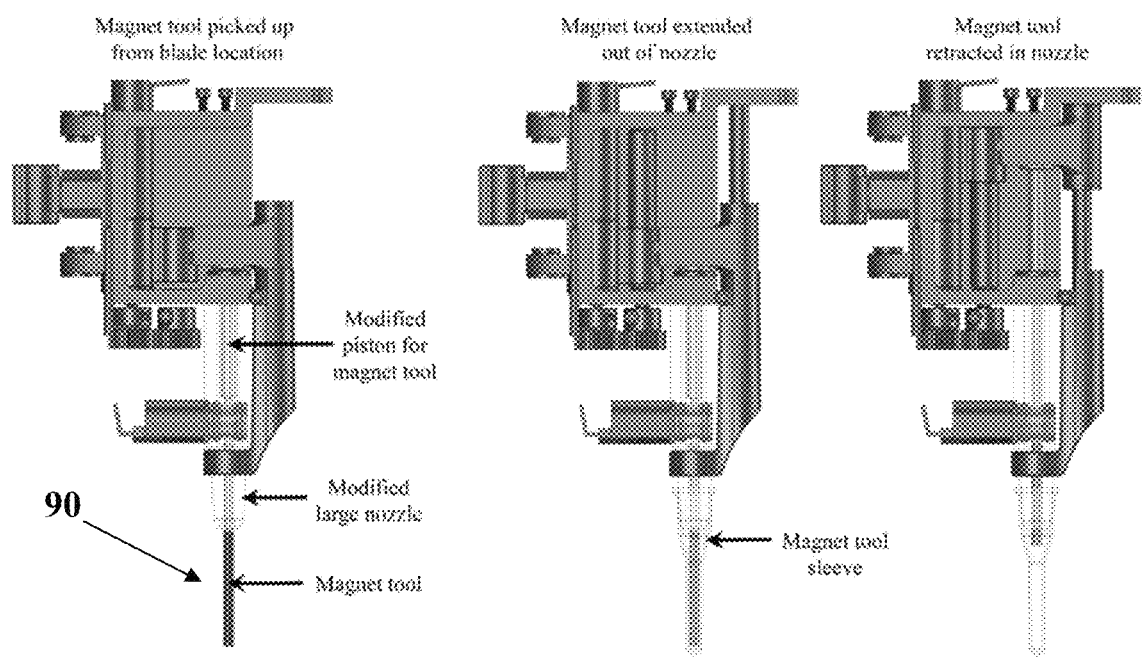
FIG. 6 show cross-sectional views of one embodiment of a sample handling apparatus with a magnet tool as described herein.

Referring now to FIG. 6, one non-limiting example of a magnet tool 90 will now be described. In this non-limiting example, one of the pipette cards in the Liquid Handling Module 60 has a modified piston assembly and nozzle to interface with the Magnet Tool 90. FIG. 6 is a side, cross-sectional view showing the Magnet Tool 90 is a magnetized rod used for separation of magnetic beads during NAA sample prep. FIG. 6 shows a side view of the Magnet Tool operation. Left: The Magnet Tool is picked up from its resting location in the device when the piston is extended out of the nozzle. The Magnet Tool secures its position onto the piston and is retracted back into the nozzle prior to pickup of the Magnet Tool Sleeve from a location on the Cartridge; Center: The Magnet Tool is shown extended out of the nozzle into the Magnet Tool Sleeve, positioned for capture of magnetic beads onto the exterior wall of the Magnet Tool Sleeve; Right: The Magnet Tool is shown retracted in the nozzle and clear of the Magnet Tool Sleeve, used in conjunction with vertical movement of the nozzle for magnetic bead release.

5. Detector 1—Luminometer Module

Figure 7:
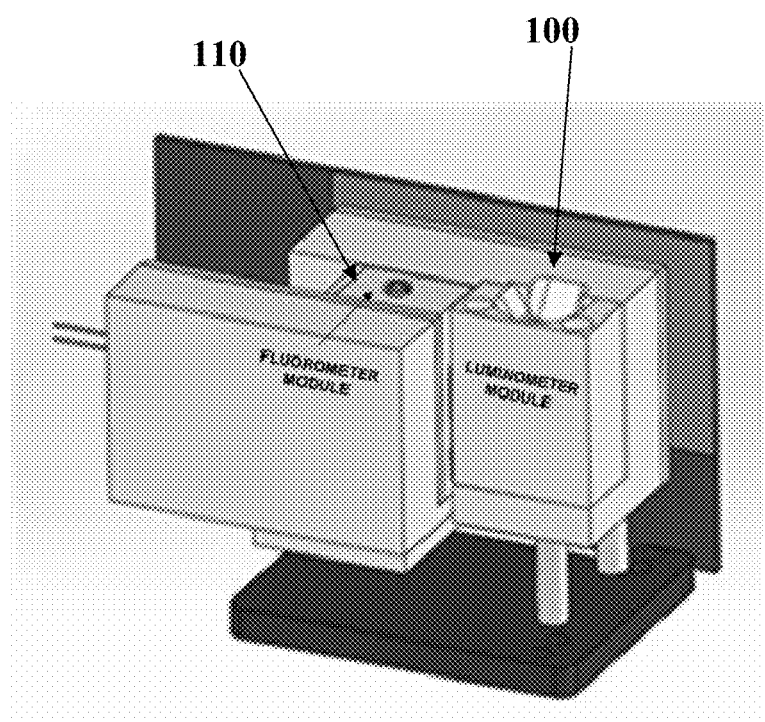
FIG. 7 shows a perspective view of one embodiment of an optical detection apparatus as described herein.

Referring now to FIG. 7, one non-limiting example of a luminometer will now be described. For at least one embodiment herein, the luminometer 100 (FIG. 7) is used for reading signals in ELISA assays. The luminometer in the present embodiment comprises of a high-gain photodiode, which has performance characteristics similar to photomultiplier tubes typically used in microtiter plate readers. The Luminometer Module includes an opening at its top through which a tip is inserted, and a detector which detects light generated as part of a chemiluminescence reaction in the tip. The luminometer can accurately detect emitted light intensity as low as ~100 photons/s.

6. Detector 2—Fluorometer Module

Referring still to FIG. 7, one non-limiting example of fluorometer 110 will now be described. The Fluorometer Module (FIG. 7) is specifically used for measuring fluorescence at an excitation wavelength band between 420 and 450 nm, with an emission band between 570 nm and 600 nm. This embodiment of the fluorometer is used for signal generation in determining the concentration of porphyrins in the LAS (for example, Zinc Protoporphyrin (ZPP), an analyte requested for measurement in military combat applications) in red blood cells. The Fluorometer Module includes a laser diode, excitation filters, and emission filters. The detector is a high-sensitivity photodiode, similar to the one in the Luminometer Module. The Fluorometer Module shares the same processor as the Luminometer Module in the SPU.

7. Detector 3—Fluorometer/Turbidimeter Module

Figure 8:
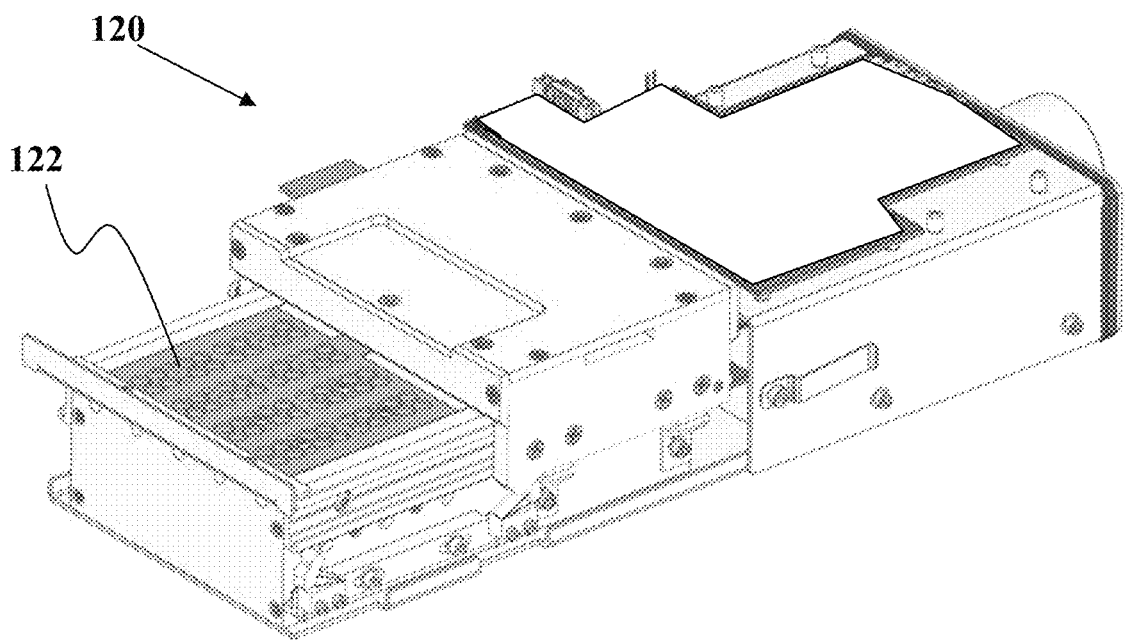
FIG. 8 shows a perspective view of one embodiment of a sample processing apparatus as described herein.

Referring to FIG. 8, one non-limiting example of a Fluorometer/Turbidimeter 120 will now be described. For at least one embodiment herein, detector 3 (FIG. 8) comprises an automated sample processing device that generates signals for assays using fluorescence and turbidity. In one non-limiting example, the core functionality of the this module 120 is the excitation and detection of emitted fluorescence from products from nucleic acid amplification reactions and the detection and measurement of light transmission through the sample for turbidity samples. The module is comprised of the following major segments: excitation signal emitter, emission signal detector, Thermal Control System, automated door, and local command printed circuit board. As part of the SPU, the SPU mechanically interacts with the module through the use of the pipette-based automated liquid handling system.

While for the current embodiment only thirty (30) wells will be used to process samples and associated controls for fluorescence measurement in the NAA Influenza assays, the circuitry and device architecture have been designed to process up to a larger number such as but not limited to 64 discrete samples simultaneously, and to work with the automated Liquid Handling Module. For at least one embodiment of the SPU described herein, sixty (60) of the individual wells 122 are used to process samples for fluorescence measurements in the LAS ("fluorescence wells"), while the remaining 4 wells are used to process samples for turbidity measurements in the LAS ("turbidity wells"). For the present non-limiting example, the turbidity wells are not used for the Influenza assays, although using for such is not excluded. It should be understood that the same hardware is used with turbidity wells as is used with the fluorescence wells with the exception of omitting filters and changing the gain values on the detector. Instead of measuring fluorescence, the turbidity wells measure light transmission through the samples over time.

For at least one embodiment of the SPU described herein, reactions in the module are supported by a Thermal Control System that is local to the module. The exclusive temperature control for this module is due to the elevated temperature requirements of the NAA reaction. The Thermal Control System is comprised of a finned heat sink, DC Cartridge heaters, fan, temperature sensors, thermal block, and heat pipes. The discrete nucleic acid amplification samples are located in vessels that rest within the thermal block, which provides a means to maintain a desired temperature within the sample. The temperature of the thermal block is monitored via two digital temperature sensors.

Optionally, the heat sink, heater, and fan system is located at the back of the device, remote to the heater block. The heat sink is connected to the heater block via water filled copper heat tubes as a means of transporting thermal energy to and away from the heater block. Air circulation is active only during cooling of the heat sink. The heat pipes allow for complete isolation of air between the thermal block where sample is present and the heat sink. This prevents contamination and aerosolization.

8. Detector 4—Spectrophotometer Module

Figure 9:
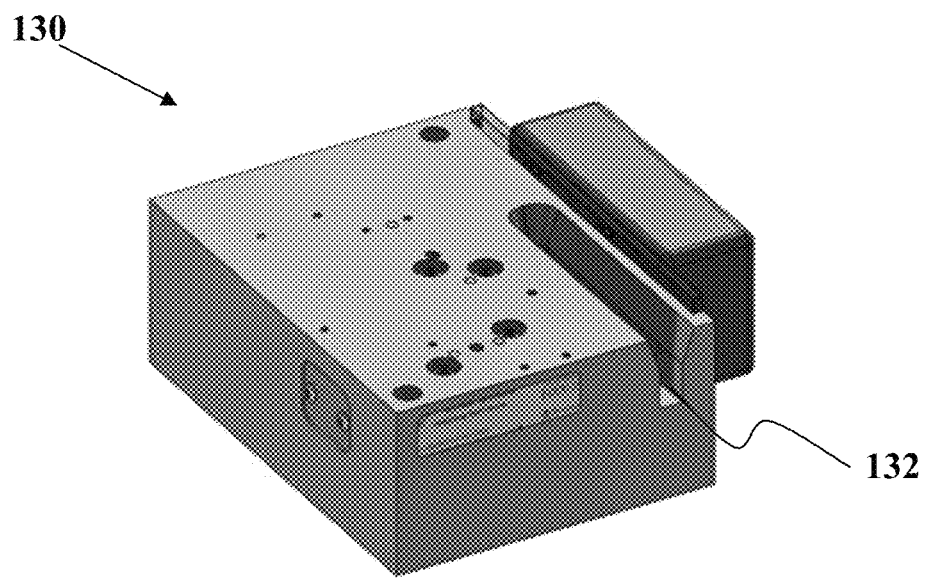
FIG. 9 shows a perspective view of another embodiment of an optical detection apparatus as described herein.

Referring now to FIG. 9, one non-limiting example of an SPU (FIG. 9) has spectrophotometric capabilities, which are provided by the Spectrophotometer Module 130, and may be used to measure absorbance of small volumes (such as but not limited to about 30 uL) of fluid samples. Some embodiments may have a linear cuvette (not shown for ease of illustration) holding defining a plurality of cavities for holding about 50 uL or less of sample in each cavity, wherein the linear cuvette may be received in slot 132. For at least one embodiment of the SPU described herein, the spectrophotometer is a compact, CCD-based spectrophotometer which can capture the complete intensity spectrum (32-bit intensity resolution, spectral range 300-800 nm, 6 nm spectral resolution) in a single capture. The output data from this module is an intensity spectrum, which is transmitted to the LAS, where the absorbance spectrum is calculated. Based on the assay, the appropriate spectral range is chosen to compute the absorbance value.

9. Detector 5—Microscopy Module

Figure 10:
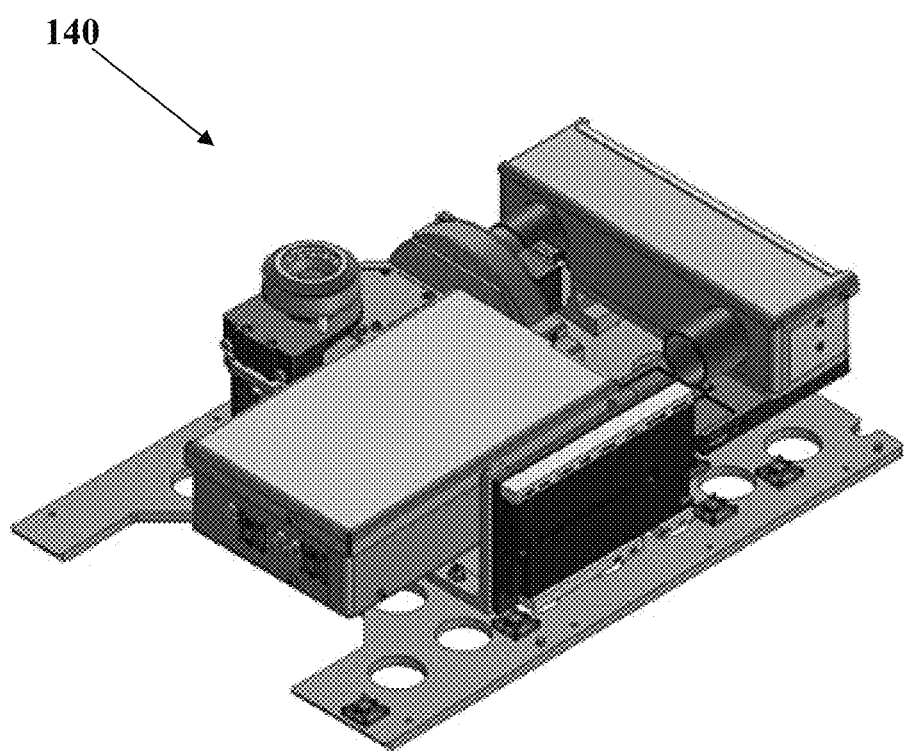
FIG. 10 shows a perspective view of another embodiment of an optical detection apparatus as described herein.

Referring now to FIG. 9, one non-limiting example of a microscopy module will be described. For at least one embodiment of the SPU described herein, the SPU has a Microscopy Module 140 (FIG. 10) for imaging cells and other cellular and non-cellular components in samples. In one non-limiting example, the Microscopy Module 140 is capable of imaging a field of view having dimensions of 473 um×410 um. Optionally, the Microscopy Module 140 is capable of imaging a field of view having dimensions of between 600 um×600 um to 400 um×400 um. In this non-limiting example, the microscopy system is capable of imaging in fluorescence and dark-field modes. The module has three laser diodes (red, green, and violet) for fluorescence, and a white ring-light for dark-field images. The sample is loaded into a cuvette which is placed on an x-y translation stage which can be actuated through stepper motors. The focal length of the objective is adjusted through a third stepper motor controlling the objective position relative to the sample. Images captured by the microscope are transmitted to the LAS for analysis.

10. Thermal Control System and Air Filter

For at least one embodiment of the SPU described herein, the SPU has precise temperature control to maintain the air temperature inside the SPU at target temperature during preparatory and processing steps. For at least one embodiment of the SPU described herein, the Thermal Control System comprises of a forced-air convection heater and three temperature sensors which are placed in different parts of the SPU. There is a closed-loop feedback controller which regulates the heater output based on temperature input from the sensors. The insulation around the SPU ensures minimal thermal exchange with ambient air.

In addition to the ambient temperature control, the SPU may have a localized heater used to bring the Cartridge up to operating temperature. In one non-limiting example, the Cartridge (see section on consumables for a more detailed description) is stored at refrigerated temperature. The sample(s) are placed in the Cartridge, and the Cartridge is introduced into the SPU. There are vents underneath the Cartridge which circulate hot air to bring the Cartridge up to the operating temperature (e.g. from refrigerated temperature to operating temperature). The heater is regulated by a closed-loop temperature controller, the input to which is a temperature sensor which is adjacent to the Cartridge.

For at least one embodiment of the SPU described herein, the Cartridge heater and the ambient heater, along with the temperature sensors and the temperature controllers, ensure that the Cartridge (containing the sample, reagents, buffers, etc.) are rapidly brought up to operating temperature and maintained at that temperature. The temperature sensors frequently record temperature across the SPU and transmit information back to the LAS for monitoring. Such environmental information is used by the LAS for accessing integrity of the operation and control of the device, maintaining quality control of the operation and control of the device, and for reducing variation or error in the data collection and sample processing performed by the device.

Optionally, the air circulated in the SPU is continuously cleaned by running it through a HEPA filter for removing particles, debris, etc. The air circulation is facilitated by an induced draft fan. The induced draft fan also maintains a slight negative pressure inside the SPU to contain the air inside the SPU.

11. Machine Vision System

For at least one embodiment of the SPU described herein, the SPU is configured to include sensors within the enclosure for the LAS to monitor device status and operation. The SPU has a camera in the enclosure for capturing whether there are bubbles, particles, fibers, particulates, debris, precipitates, or other anomalies associated with any tips or vessels being handled within the SPU which may affect readouts. The SPU camera also captures images of components that can be used to determine whether the components are positioned properly, or where components are positioned. Imaging can be used to allow the LAS to assess if a volume of sample, reagent, or other material falls within a desired range, or whether a sample, reagent, or other material is located in a desired location. This information is frequently communicated to the LAS for error-checking, calibration, protocol execution, and quality control of the SPU.

Software, Touchscreen, and Process Work Flow

For at least one embodiment of the SPU described herein, the SPU operates under the control of the LAS. In this non-limiting example, the SPU is connected to the LAS via a secure Internet or other data network connection, and the SPU and LAS are capable of two-way communication with each other. For example, the LAS can send various commands and protocols to the processor of the SPU, for execution by the SPU. Similarly, the SPU can send information obtained by the SPU to the LAS, such as data obtained from pre-analytic steps with a sample or information obtained from sensors within the SPU (e.g. signal, image, temperature information). Information sent by the SPU to the LAS may be in response to a specific request for information from the LAS to the SPU, or it may be part of a standardized protocol. Upon completion of pre-analytic processing in the SPU, the LAS performs analysis and post-analytic processing.

Although for at least some embodiments herein, an SPU may be situated at a CLIA-certified laboratory Patient Service Center location which is physically separate from the LAS, complete control and oversight is extended from the central LAS to the remote SPU to ensure CLIA-oversight and certification of the tests being reported. The SPU serves as part of The CLIA-certified laboratory, and laboratory results generated from data analyzed in the LAS and obtained from a sample processed on a SPU are CLIA-certified.

Optionally, at least some embodiments may have a touch screen embedded in the SPU for operation of the device and/or other functions of the system. The touchscreen allows for detailed, user-oriented instructions, oversight, by ensuring a technician follows all appropriate steps before processing a sample, and two way communications. Operation of the SPU at a PSC is performed by a—certified phlebotomist or other appropriately state-licensed technician; the technician is trained in The CLIA-certified laboratory and is managed by a laboratory director. In addition, the—trained technician at The PSC runs quality control (QC) Cartridges on the SPU at regularly scheduled intervals by pressing a button on the SPU touchscreen, placing a Cartridge inside the SPU, and pressing the touchscreen button again (no other steps are required). Data from the QC Cartridges are sent from the SPU to the LAS, where the data is analyzed to monitor the operation of the SPU and to alert The CLIA-certified laboratory to take any action as necessary.

In accordance with at least one embodiment herein, the LAS allows the operation of the clinical laboratory process without operator intervention, including control of the SPU through direct LAS interfacing, specimen manipulation, transportation of the specimen and related signals, result evaluation, repeat testing, reflex testing and quality assessment and results reporting.

For at least one embodiment of the SPU described herein, the secure network infrastructure allows for CLIA-compliance for certified analysis and testing through the LAS for determination of the presence or absence of various substances in the human body in CLIA-certified laboratory while automating sample processing in field through the SPU in PSCs to minimize pre-analytic error and variability.

Consumables and Materials

For at least one embodiment of the SPU described herein, the sample, as well as products of further processing and reaction are contained in disposable consumables inside the disposable reagent tray or Cartridge. Optionally, they are configured to be placed onto the disposable reagent tray. Optionally, thee sample and any other consumable are held, supported, or contained by a physical object with the form factor for locating the items in a consistent position in the SPU. This, in part, allows for repeatable control of the system. Optionally, the consumables are designed to replicate the processing receptacles used in the relevant traditional 'gold-standard' assay protocols. All consumables are discrete such that reagents and reactions for each assay reside and occur, respectively, in physically separate locations to prevent cross-reactivity. The consumables contain all liquids or reagents such that no sample or reagent ever directly interacts with the device. All consumables for processing are contained in the Cartridge (and are not built into the SPU) and are placed back into the Cartridge at the completion of processing for disposal.

Figure 11:
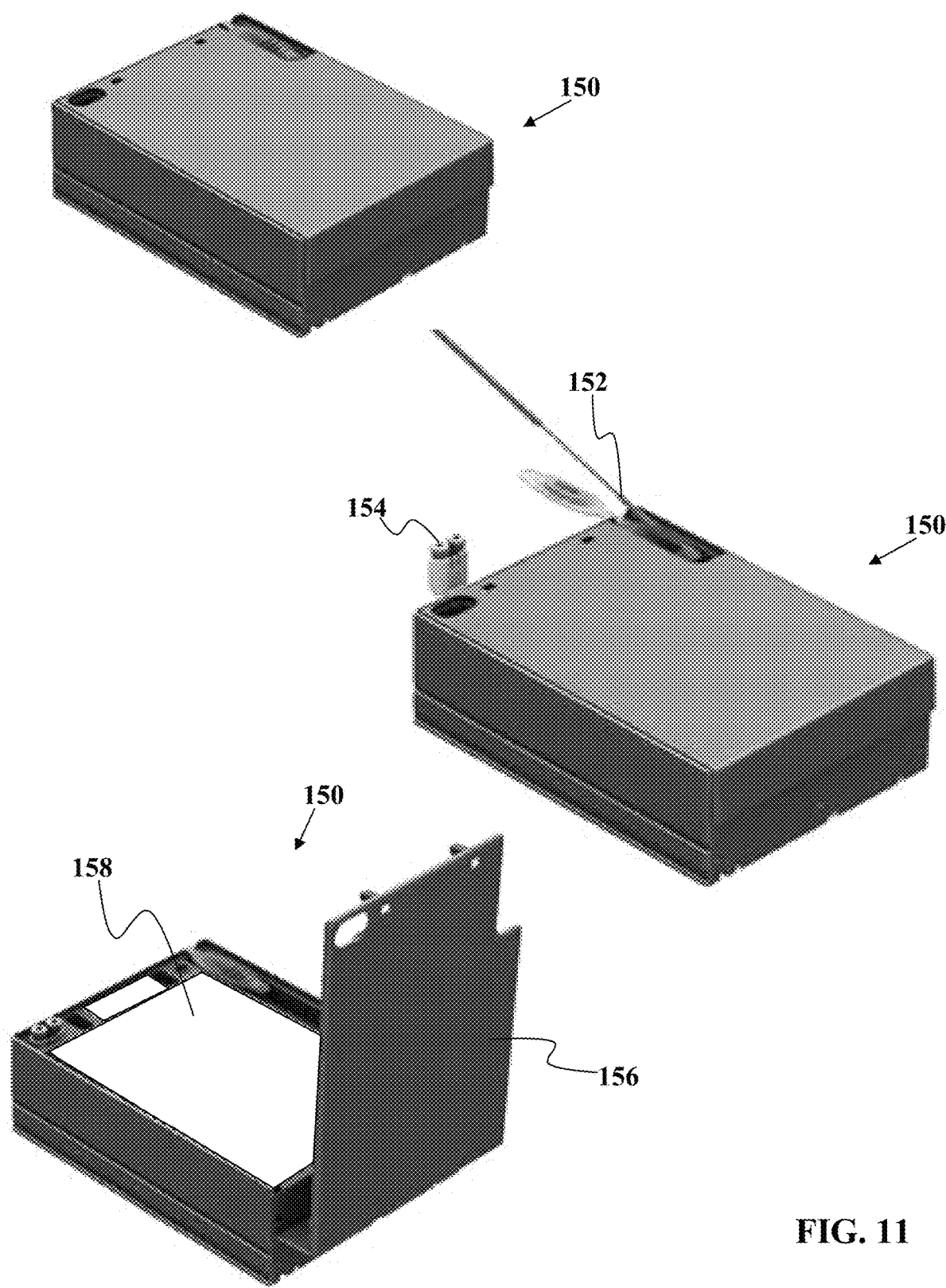
FIG. 11 show perspective views of one embodiment of a cartridge as described herein.

FIG. 11 shows one embodiment of the Cartridge 150 in various configurations. Left: Closed cartridge. Center: Samples (Swab 152 with nasal, oral, or other sample and SCU 154 with blood sample) being introduced into cartridge. Bottom: Cartridge with lid 156 open inside the SPU.

For at least one embodiment of the SPU described herein, the consumables used for the NAA and ELISA assays may include the following listed below that may be in a support structure such as but not limited to a cartridge. Optionally, some embodiments of the cartridge may have all of the different types of vessels and tips listed below in the cartridge. It should be understood that some embodiments may have different volume capacity than those listed below. In one embodiment, the max volume fill level is in the range of about +/−50% of the amounts listed. Optionally, the max volume fill level is in the range of about +/−40% of the amounts listed. Optionally, the max volume fill level is in the range of about +/−30% of the amounts listed. Optionally, the max volume fill level is in the range of about +/−20% of the amounts listed. It should be understood that some embodiments may have different max volumes even for vessels or tips of the same type. It should be understood that some embodiments may not have all of the different types of vessels and tips listed. In one embodiment, the cartridge contains no more than two types of the items listed. Optionally, the cartridge contains no more than three types of the items listed. Optionally, the cartridge contains no more than four types of the items listed. Optionally, the cartridge contains no more than five types of the items listed. Optionally, the cartridge contains no more than six types of the items listed. Optionally, the cartridge contains no more than seven types of the items listed. Optionally, the cartridge contains no more than eight types of the items listed. Optionally, the cartridge contains no more than nine types of the items listed. Optionally, the cartridge contains no more than ten types of the items listed. Optionally, the cartridge contains no more than eleven types of the items listed below. These can be held in a matrix or other pattern in the area 158 of the cartridge.

Round vessels—60 uL capacity polypropylene vessels for storing reagents, dilutions, mixing, and reactions.

Wash vessels—200 uL capacity polypropylene vessels for storing wash buffers.

Mini tips—10 uL capacity polypropylene tips for transporting fluids; with silica filters for preventing cross-contamination.

Large tips—40 uL capacity polypropylene tips for transporting fluids; with silica filters for preventing cross-contamination.

ELISA tips—10 uL capacity coated polystyrene tips for ELISA binding reactions; with silica filters for preventing cross-contamination.

NAA vessels—60 uL capacity polypropylene vessels which serve as reaction vessels for the amplification reaction. The final fluorescence signal (from the product generated in these vessels) is detected from these vessels.

NAA trays—Trays which hold 8 NAA vessels. The trays can also be picked up by the fluid handling module to transport the vessels between the Cartridge and the NAA module.

Sonicator vessel—350 uL polystyrene vessel, used to contain sample during sonication.

Magnet Tool Sleeve—disposable polypropylene sleeve separates magnet from consumable to prevent contamination.

Swab vessel—400 uL capacity polypropylene vessel designed to contain the nasopharyngeal swab.

Nanotainer tube—100 uL capacity PETG vessel into which blood samples are introduced.

Sample Collection Unit (SCU)—PETG container which houses the Nanotainer tubes, and interfaces with the cartridge.

Cartridge—Houses all consumables listed above. Secured by a lid to hold all consumables in place and prevent user interaction.

Optionally, the Cartridge comes with a closed lid (FIG. 11, Left), under which are all pre-populated consumables required for the NAA and ELISA assays. Regents and buffers required for the assays are pre-filled and sealed in Round vessels and Wash vessels. The ELISA tips are pre-coated with the capture antibody specific to the particular assay. Optionally, the NAA vessels come pre-filled with the master mix for the assay, followed by a protective wax layer on top.

Only the sample entry port(s) on the Cartridge are exposed to the certified phlebotomist or appropriately state licensed sample collection technician. FIG. 11 Center shows a cartridge in which both the blood sample and the swab sample are being introduced.

The nasopharyngeal swab is placed directly inside the accessible Swab vessel on the Cartridge, which is pre-filled with a transfer medium. The lid to the swab vessel is closed after introduction of the swab.

Once collected, blood samples are collected in Nanotainer™ tubes, which in one embodiment has been separately registered as a sample transport containers.

The SCU is then placed in the Cartridge (FIG. 11, center). The Cartridge is then inserted into the SPU, and the cartridge is drawn in, the door to the SPU is closed, and the lid is opened by means of a mechanism inside the SPU. This exposes all consumables (FIG. 11, Right) inside the SPU. Following this, the sample processing, reagent addition, and signal generation steps take place in the SPU, as instructed by commands from LAS.

After completion of the appropriate processing steps, a Cartridge is ejected with the lid closed, and can be appropriately disposed of in its entirety in The Patient Service Center.

Scientific Basis

The SPU and LAS were designed to automate the exact processing steps and protocols associated with the most precise and accurate CLIA-certified test methods. The SPU is configured to automatically perform a wide range of standard laboratory sample processing steps, such as pipetting, sonicating, mixing, and heating. These steps may be automatically performed by the SPU in accordance with a protocol executed by a processor on the SPU that received commands from the LAS. Automation of the laboratory sample processing steps permits the steps to be performed by the SPU with very high accuracy and precision targeted to exceed that achieved by human technicians for the same sample processing steps. In addition, the SPU is capable of performing customizable sample processing steps (e.g. variable pipetting volumes, sonication times, etc.), based on the specific instructions of a given protocol from the LAS.

Device Manufacturing and Materials

It should be understood that the device may be assembled in a GMP environment from a variety of commercially available components, fabricated electrical assemblies, cable assemblies, sheet metal structures, and machined mechanical parts. All component inventory is managed through supply chain group using an ERP system. All parts, except for the commercially available components, are fabricated based on designs. Most machined parts are produced at internal machine shop.

When building a module, components are kitted and transferred to the assembly group. The assembly technicians assemble the module per a Manufacturing Operating Procedure (MOP) document. MOPs are developed by manufacturing engineers, reviewed by design engineers, and officially released into a controlled system for revision management. Once assembly is complete, modules are subjected to a functional checkout to verify functionality.

Manufacturing and production are performed in accordance with QSR, following The Quality System, which is drafted for compliance with the applicable Code of Federal Regulations ("CFR") provisions.

Laboratory Automation System

The LAS comprises at least one server configured to communicate with and control one or more SPUs with an encrypted, certificate-based security system. The LAS provides a number of functions, including sending test protocols to the SPU based on the desired tests to be run on the sample and for maintaining oversight over the SPUs. During processing, the SPU and LAS are communicating to validate the quality and integrity of the consumables, based on lot information tracked in the LAS, execute the sample processing steps, and monitor and oversee the quality of the sample processing. After controlling sample processing in the SPU, signal sets from the sample are transferred to the LAS where the raw data is analyzed, the relevant reportables are generated for a Laboratory Information System, and post-analytic processing steps are performed.

Optionally, the LAS is run in and overseen by CLIA-certified laboratory, and provides oversight and remote control of the SPU. The consumables containing patient samples (Swab vessel for nasopharyngeal swab and Nanotainer tube for blood sample) are placed in a Cartridge and introduced into the SPU. The SPU scans a barcode on the Cartridge, and the barcode value is transmitted to the LAS, which securely de-codes the barcode value, and sends a sample processing protocol to the processor in the SPU. The processor further distributes tasks received from the LAS to various modules in the SPU. The SPU constantly feeds information back to the LAS to ensure constant monitoring of the SPU and its performance. The final steps of sample processing are signal generation (which is chemiluminescence light in the case of the ELISA assays, and fluorescence light for the NAA assays), and signal detection by detectors (Detector 1 for ELISA and Detector 3 for NAA). The detectors generate a set of 16-bit integers, the magnitudes of which are proportional the generated signal. These sets of integers are the output from the SPU, and are transmitted back to the LAS, which performs analysis on these raw integer sets and associated values indicating performance of replicates, controls, calibrators, QC tests, and any outliers, and yields clinically relevant analyte reportables for CLIA laboratory staff to oversee and further analyze, as applicable.

Nucleic Acid Amplification (NAA) Assay for Influenza Detection

Figure 12:
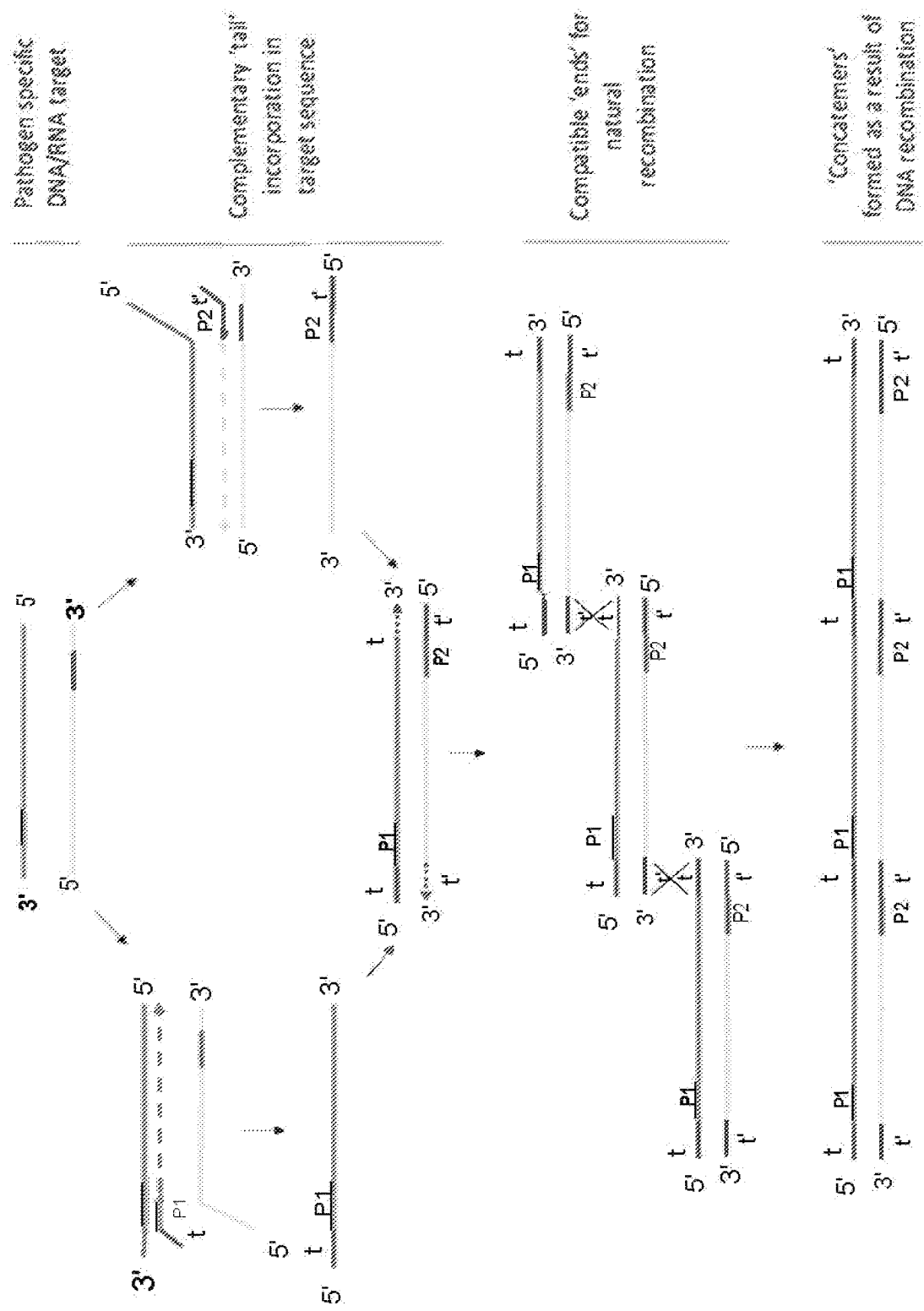
FIG. 12 describes one embodiment of a nucleic acid amplification method as described herein.

NAA Chemistry:

Referring now to FIG. 12, a Nucleic Acid Amplification (NAA) assay schematic of one amplication technique is shown. By way of non-limiting example, the present embodiment of the NAA comprises an isothermal method that provides rapid qualitative detection and identification of pathogens from clinical samples.

NAA Principle: in one non-limiting example, NAA harnesses the power of DNA recombination which is facilitated through primer design during the course of Nucleic Acid Amplification. The NAA reaction is of an exponential nature and can be observed using DNA intercalating fluorescent dyes, nucleic acid probes, etc. in real-time. The data can be interpreted to detect the presence or absence of pathogen-specific genetic material in a given sample. FIG. 12 shows a schematic diagram of the NAA method.

In this example, amplification is done on a selected DNA/RNA target which is specific to the target pathogen. The brown and yellow lines represent the two strands of duplex DNA whereas the green and purple part is the selected region against which the primers are designed. The two primers (P1 and P2) used in the amplification process are shown as green and purple arrows with red 'tails'. Tails (t and t') on the 5' end of the primers are complementary sequences of each other. During the initial amplification cycles, the tails t & t' are incorporated in the product DNA strands. This process generates duplex DNA molecules with homologous ends that can go through natural recombination (cross-over sites demonstrated by 'X' mark) as is seen in nature during DNA replication. Recombination results in the formation of concatemers' of DNA molecules that grow in molecular size with each cycle of amplification. The replication of DNA concatemers in the presence of primers results in amplification of target nucleic acid at an exponential rate, which can be observed in real-time using DNA intercalating fluorescent dyes.

Protocol for Influenza NAA Assays

Viral Nucleic Acid Extraction

Figure 13:
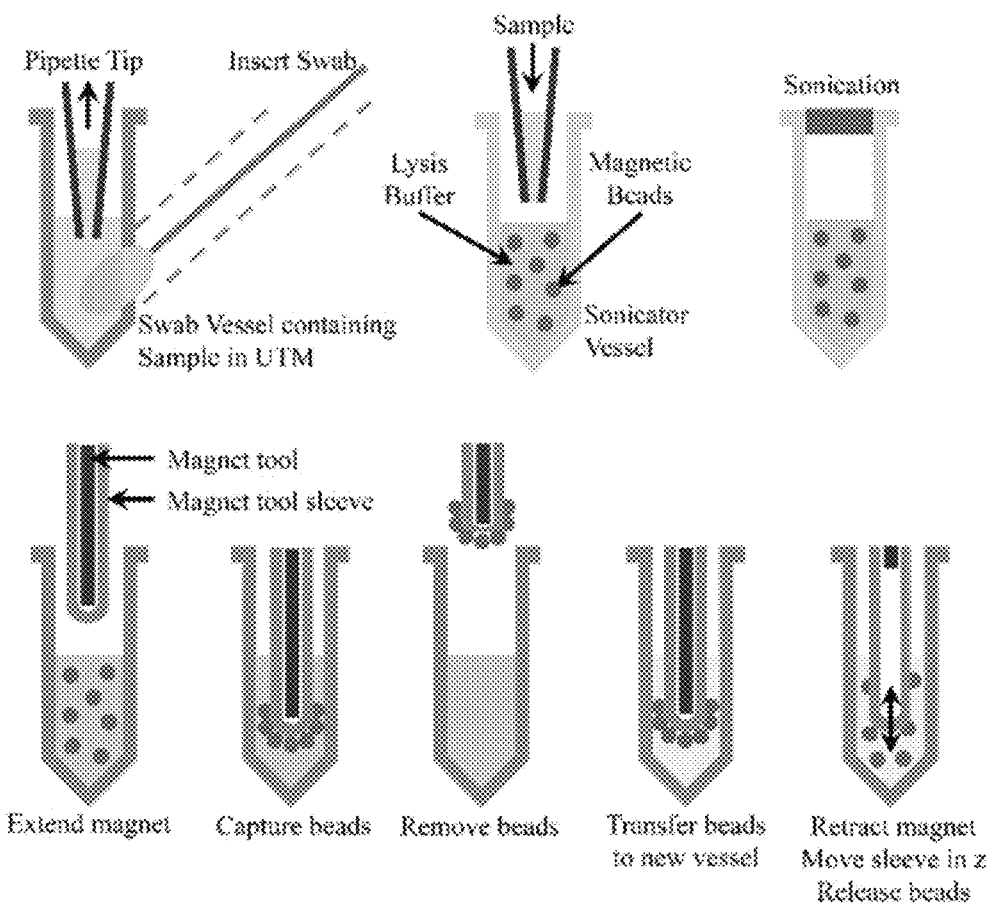
FIG. 13 describes one embodiment of a magnetic bead-based method as described herein.

Referring now to FIG. 13, one non-limiting example of NAA nucleic acid purification steps in the SPU will be described. A certified CLIA-laboratory (and appropriately state licensed sample collection) technician takes a Swab vessel which comes sealed with a lid at the swab port. The technician removed the lid, inserts the flocked swab sample into the Swab vessel embedded in the Cartridge, which contains an aliquot of universal transport medium, separates the swab from the plastic handle at the defined breakpoint in the handle, and re-closes the lid. The majority of the sample on the swab immediately releases into the medium upon contact. The vessel containing the swab is then capped, and the Cartridge is ready for processing with the device. The Influenza NAA assay begins with sample being transferred from the Swab vessel by a Large tip into the Sonicator vessel.

Optionally, the nucleic acid extraction implemented in the SPU utilizes a magnetic-bead based methodology to isolate and purify nucleic acids from a sample matrix. A brief overview of the steps involved are as follows:

1) Optionally, a Large tip is inserted into the access point on the Swab vessel, breaking through a foil seal barrier to access the sample. The sample is mixed by pipetting up and down for several cycles to ensure sample release from the swab through agitation of the surrounding fluid.
2) Optionally, the sample is transferred from the Swab vessel to the Sonicator vessel by means of two large pipette tips, and lysis buffer and functionalized magnetic beads are added to the Sonicator vessel from other reagent storage locations on the Cartridge.
3) Optionally, the Sonicator vessel is moved to the sonicator probe location, and the vessel is sonicated in order to lyse open the cells to release the nucleic acids. The sonication vessel is returned to its location on the Cartridge after this step.
4) Optionally, binding buffer, which helps the nucleic acids bind to the functionalized magnetic beads, is transferred from a reagent storage well to the Sonicator vessel and mixed by pipetting up and down.
5) Optionally, a Magnet Tool that resides inside the SPU is picked up using a large pipette nozzle. The Magnet Tool is retracted inside of the nozzle such that only 2-3 mm is visible before that nozzle is used to pick up the Magnet Tool Sleeve in the consumable. This sleeve shields the Magnet Tool from the sample to prevent contamination.
6) The Magnet Tool is then extended into the tip sleeve and inserted into the Sonicator vessel to capture the magnet beads on the exterior of the sleeve.
7) Optionally, magnetic beads with captured nucleic acids aggregate on the tip of the sleeve and can be transported into a well containing wash buffer.
8) The Magnet Tool is retracted into the nozzle, and the entire nozzle is moved in vertical directions for several cycles to release the beads and mixed by fluid displacement using a piston motion.
9) The Magnet Tool is extended back into the tip sleeve and inserted into the wash buffer well to capture the washed magnet beads and transport them to the next step.
10) For each additional bead wash to purify the sample, steps 7 through 9 are repeated.
11) The Magnet Tool and its sleeve carrying captured magnetic beads with purified nucleic acid sample is inserted into the elution well.
12) The Magnet Tool, covered by the Magnet Tool Sleeve, is retracted into the nozzle by moving the piston motor, and the nozzle is moved in a vertical direction multiple times to release the beads and mix them with the fluid. The Magnet Tool/Magnet Tool Sleeve assembly is removed from the well by moving the nozzle.
13) The released beads are allowed to incubate in the elution well for 1 minute.
14) The Magnet Tool is extended back into the Magnet Tool Sleeve and inserted into the elution buffer well to capture the magnetic beads. The Magnet Tool Sleeve is then discarded into its original location on the Cartridge and the Magnet Tool is returned to its resting location in the SPU.
15) The elution buffer is ready to be distributed into the downstream NAA assays.

NAA Assay and Signal Generation

For at least one of the embodiments described herein, the elution buffer extracted from the steps above contains the extracted nucleic acid material. In one non-limiting example, Detector 3 is brought up to 56° C. utilizing the module's thermal controller. The NAA tray with the NAA vessels is picked up by the Liquid Handling Module and transferred to Detector 3. The vessels contain the master mix for the NAA assay, capped with a wax layer. This wax layer melts at the elevated (56° C.) temperature. 3 uL of elution buffer is aspirated from the elution well on the Cartridge and transferred into the NAA vessel using a Mini tip, ensuring that the tip penetrates past the molten wax layer. The sample is mixed with the master mix to ensure homogeneity. The tip is discarded back into the Cartridge. When the tip is moved away from the detector module, the lower temperature of the SPU causes the molten wax around the tip to solidify, thereby forming a physical barrier around the tip opening and preventing any sample from leaking out of the tip. This protects against contaminating the SPU. A new tip is picked up by the Liquid Handling Module, and 2 uL of enzyme is transferred from a reagent well in the Cartridge to the NAA vessel, and is mixed with the sample and the master mix. The tip is retracted and returned back to its location on the Cartridge.

Optionally, the reaction mixture in each NAA vessel is incubated for 5 minutes, after which the photodiode corresponding to each reaction vessel is used to capture the reaction signals at 30 s intervals for a period of up to 30 min. The data (in the form of counts) is transmitted in real time to the LAS, where the fluorescence signal is recorded and analyzed in real-time. The analysis comprises of identifying a change point to determine the inflection time of the assay.

Example of System TNAA Operation

In this non-limiting example, a detailed overview of how the SPU executes a protocol for running a panel of NAA tests. This example helps demonstrate how the SPU automates pre-analytic sample processing substantially reducing human error in sample preparation, extraction, and processing, and for reducing variability and errors in test results.

In this non-limiting example, a processing module is provided as part of the SPU and is designed to automate the manual steps may be done in a laboratory. Some embodiments may use more than one processing module to process a single sample. Optionally, multiple samples are simultaneously processed by multiple modules in the same SPU. This method minimizes human error in typical lab handling practices.

One embodiment may have a pipette, a detector module, and a barcode reader as part of the SPU. In this example, the SPU can be configured to accept a single-use, disposable that contains a plurality of different types of vessels and/or tips in the disposable. [ ]

At the start of the process, a flocked nasal swab is inserted by the technician into a disposable such as a cartridge or other container. The cartridge may have a plurality of different types of vessels, tips, assay units, and/or reagent units in the cartridge. The swab vessel is filled with an amount of universal transfer medium (UTM) such as about 200 uL to about 300 uL of universal transfer medium (UTM). UTM is available from a plurality of manufacturers including Millipore, Copan, or the like. The cartridge with the sample can then be loaded into the SPU. Note that in some embodiments, the cartridge may have a lid covering at least one surface of the cartridge that is openable by the SPU using a tool such as but not limited to a key, pin, pushrod, or other item that allows the lid to only be easily opened when the cartridge is in the SPU. This can deter tampering of the cartridge when it is not in the SPU.

In one non-limiting example, all reagents and consumables used to process the sample come pre-loaded and sealed on the cartridge. Optionally, not only are the reagents and consumables on the cartridge for a certain set of assay(s), the cartridge may contain additional reagents and/or consumables that duplicate at least some of the reagents and/or consumables for that assay. This can provide for redundancy and/or the ability to run additional assays. Optionally, the additional reagents and consumables are different for those for the certain set of assay(s), thus allowing a single cartridge to be able to run additional assays others than those for that certain set. In this manner, some embodiments may have a cartridge that is configured to be generic that can cover a plurality of different types of assays. Some embodiments are configured for holding a plurality of different samples from the same subject. Some embodiments are configured for holding a plurality of blood samples from the same subject. Optionally, some embodiments only have a single sample from the same subject. Optionally, some embodiments have multiple samples from multiple subjects in a cartridge. Optionally, some embodiments have multiple different samples from multiple subjects. Optionally, some embodiments have multiple same type of samples, such as but not limited to blood, from multiple subjects.

Optionally, some embodiments of the SPU can be configured to use multiple cartridge to process a sample. Optionally, some alternative embodiments of SPUs may have a module that contains certain specific materials such as diluents, certain commonly used reagents, or the like that is kept on-board and not part of the cartridge. In such an example, the on-board materials can be used in combination with reagents and/or consumables on the cartridge.

In one embodiment, the cartridge may be a single-use cartridge. In one embodiment, the cartridge is disposed of with any used items therein. Optionally, the cartridge is one time use but is then cleaned and repackaged for use, wherein content therein can be disposed of, but the frame portion of a cartridge can be cleaned, sterilized, and used again. It is contemplated that the various aspects of the cartridges described herein may be fabricated from materials known in the art or developed in the future such as but not limited to aluminum, chromoly steel, titanium, polymer, plastic, the like, or single or multiple combinations of the foregoing.

In this non-limiting example, the SPU can be configured to read the barcode on the cartridge and then automatically downloads the appropriate protocol from a data storage such as but not limited to a server, a remote computer, a Laboratory Automation System (LAS), and/or combinations of the foregoing. In one non-limiting example, multiple cameras and sensors in the device are used throughout the protocol to assist to ensure error-free operation.

From the front view, one can see a liquid handling module such as but not limited to a pipette or arrays of pipettes above the cartridge.

In this non-limiting example, an NAA protocol begins with several nucleic acid purification steps. In brief, this specific example of nucleic acid extraction is implemented in the SPU using a magnetic-bead based methodology to isolate and purify nucleic acids from the sample matrix. It should be understood of course that other embodiments not based on beads is not excluded. For example, some embodiments can use vessels or other materials for NAA instead of a bead based system.

As part of this example of NAA sample processing, a first pipette tip is pick-up by the pipette nozzle from the pipette assembly. One embodiment may have a plurality of pipette nozzles. Optionally, some may have more nozzles for a lower volume of fluid and fewer nozzles for handling a higher volume of fluid. In this non-limiting example, a filter located across an upper portion of the tip is one of several measures implemented to prevent cross-contamination, particularly when the nozzle is used to repeatedly engage clean and dirty tips in a roughly sequential manner.

After appropriate materials are brought by various pipette tips and deposited in a mixing vessel, which may or may not be part of the cartridge, the combined lysis and binding buffer is first aspirated and dispensed by the pipette into a sonicator vessel. Note that Sonication is not necessarily needed for this panel of tests but it can be used to disrupt tougher pathogens. Also note that for other assays, lysis and binding buffers may be added at discrete times in the protocol to enhance the extraction process. Finally, for an NAA-only cartridge, i.e. no ELISA, there may be the option of loading a lysis buffer directly into the swab vessel. Although not limited to this, UTM is primarily for having the option of running ELISAs on the swab sample and/or shipping/storage purposes. It should be understood that UTM can also be used for other purposes and those are not excluded herein.

As part of this example of NAA sample processing, a large pipette tip may be inserted into the access point on the Swab vessel, breaking through a foil seal barrier to access the sample from the swab. In this non-limiting example, the sample is mixed by pipetting up and down for several cycles to ensure sample release from the swab through agitation of the fluid. As seen, some cartridges can have the swab inside the vessel. This avoids manual mixing and in doing so, getting more consistency. Optionally, the sample is transferred from the Swab vessel to the sonicator vessel in two steps.

As part of this example of NAA sample processing, functionalized magnetic beads are added to the sonicator vessel from a sealed reagent vessel on the cartridge after pre-mixing. In this non-limiting example, the beads are mixed with the sample. After mixing, then the tip is dropped off. As seen for this example, the nucleic acids from the sample lysate become selectively bound to the magnetic beads, which allows their isolation from the sample matrix with high efficiency.

As seen for this non-limiting example, a magnet tool (that resides inside the SPU) is picked up using a large pipette nozzle. The Magnet Tool is retracted up into the nozzle before that nozzle is used to pick up the Magnet Tool Sleeve. Optionally, this Sleeve shields the Magnet Tool from the sample to prevent cross-contamination.

Optionally, the Magnet Tool may then extended into the Magnet Tool Sleeve and be inserted into the sonicator vessel to capture the magnet beads on the exterior of the Sleeve.

Optionally, the magnet tool may be pulled out of the sample, extracting the magnetic beads with captured nucleic acids aggregated on the tip of the sleeve, and transporting it into a well containing extraction buffer. In this non-liming example, the Magnet Tool is retracted into the nozzle, releasing the beads, and the entire nozzle is moved up and down for several cycles to release the beads and mix them. Exposure to the elution buffer causes the bound nucleic acids to release from the magnetic beads into the elution buffer.

Optionally, the Magnet Tool may be extended back into the tip sleeve and inserted into the wash buffer well to capture the magnet beads. After this bead extraction, this well contains only purified nucleic acids.

Optionally, the beads may be dropped off into another vessel by raising the Magnet Tool away from the beads and agitating by a vertical mixing motion.

Optionally, the Magnet Tool Sleeve and Magnet Tool are then placed into their original locations on the Cartridge. In some embodiments, the magnet tool may be dropped off in the device. For the purpose of this video and for clarity, we drop off the magnet tool in the cartridge.

Optionally, another large pipette tip is picked up, and the eluted sample is aspirated into the tip. The extracted nucleic acid sample is then dispensed into multiple vessels. Some embodiments may drop of into two or more vessels. Some embodiments may drop of into three or more vessels. Afterwards, the tip is dropped off.

Meanwhile, Detector 3 (Fluorometer/Turbidimeter) has been brought up to a higher than ambient temperature. In one embodiment, this may be in the range of about 50° C. to 60° C. utilizing the module's thermal controller. Some embodiments may use 56° C. The door on Detector 3 opens. The TNAA tray with the TNAA vessels is picked up by the Liquid Handling Module and transferred to Detector 3. These vessels are preloaded with master-mix/primers and a wax barrier. This wax layer melts at the elevated (56° C.) temperature.

Optionally, three Mini-tips with filters may be picked up by the pipette assembly.

Optionally, single digit number of microliters of extracted sample are aspirated from the elution well on the Cartridge and transferred into NAA reaction vessels, ensuring that the tip penetrates through the molten wax layer. Optionally, the sample is dispensed into the master mix.

When the tip is moved away from the detector module, the lower temperature of the SPU causes the molten wax around the tip to solidify, thereby forming a physical barrier around the tip opening and preventing any sample from leaking out of the tip. This protects against cross-contamination. Optionally, the tips are discarded back into the Cartridge. Some embodiments may use a master mix—premixed, stable select primer probes, buffers, substrates used for NAA.

Optionally, three more mini-tips with filters are picked up. And extracted sample is again transferred to NAA reaction vessels in the same manner. (This process occurs 8 times as when running 24 TNAA tests on the sample in this protocol.

After the foregoing, three Mini-tips with filters are picked up and single digit number of microliters of enzyme is transferred from a reagent well in the Cartridge to the NAA vessels, and is mixed with the sample and the master mix. The tips may be retracted and returned back to their locations on the Cartridge. Again, wax protects against cross-contamination. This process is repeated for all 24 reaction vessels.

After all of the above, the door of Detector 3 is closed. Some embodiments may not use doors. The reaction mixture in each NAA vessels is incubated for 5 minutes, after which the photodiode corresponding to each reaction vessel is used to capture the reaction signals every 30 seconds for 30 minutes. In one non-limiting example, the data (in the form of counts) is transmitted in real time to the LAS, where the fluorescence signal is recorded and analyzed in real-time. Optionally, other embodiments may send data in other forms such as signal strength, electrical output, or other representation of the signal being detected. Optionally, the analysis may comprise of identifying a change point to determine the inflection time of the assay. The data is processed and analyzed under the overview of CLIA lab.

After the reactions are done, the door of Detector 3 is opened. The three NAA vessel trays (which in this example, each carries eight assay units) are returned to the cartridge. Optionally, the wax solidifies over the amplified products preventing any cross-contamination. The Detector 3 door is closed and the pipette is parked in its rest position. The device can prompt the user that the protocol is complete, at which time the cartridge can be removed from the device and discarded appropriately. For other embodiments such as for non-disposable cartridges, other post-processing steps are followed to handle used materials and reagents.

ELISA Assay for Influenza Antibody A and B (IgG and IgM)

ELISA Principle

Optionally, the Influenza AB antibody immunoassays are similar in principle to a classic microtiter plate based immunoassay, with the primary difference being the capture surface geometry and automated LAS control. The microtiter plate in a standard immunoassay is replaced by a tip, the surface on which the analyte of interest is captured. The quantity of bound analyte is determined by a chemiluminescent reaction involving the enzyme alkaline phosphatase (ALP) in the presence of substrate. The chemiluminescence signal is read in a Luminometer Module, which is similar in performance to photomultiplier tubes (PMTs), used in microtiter plate readers for ELISA assays. The output from the SPU is a count, similar to the photon counts produced by a PMT.

The Influenza antibody assays comprises of IgG and IgM ELISA assays each for Influenza-A and Influenza-B. All four assays follow a typical sandwich ELISA format. Anti-Influenza antibodies present in sample (whole blood, plasma, or serum) bind specifically to the inactivated native Influenza antigen on the capture surface. The bound human anti-Influenza antibodies are detected by an Alkaline Phosphatase (AP) labeled mouse monoclonal antibody (detection antibody), which binds to human antibody (IgG or IgM). The bound complex is incubated with AP substrate to initiate the chemiluminescence reaction. The rate of the chemiluminescence reaction (which is proportional to the AP concentration, and hence the anti-influenza antibody concentration), generates light levels in the Luminometer Module, which are transmitted to the LAS to be read for analysis.

Protocol for Influenza Antibody ELISAs

For at least one of the embodiments described herein, the antibody ELISA protocol uses whole blood, plasma, or serum as a starting sample. The following is the sequence of steps for the antibody assays:

1. A Large tip is picked up, and 18 uL of diluent is transferred from the Wash vessel to 4 Round vessels. The tip is ejected back in the Cartridge.
2. 4 Mini tips are picked up, and 2 uL of sample is aspirated in each tip, and dispensed into the 4 Round vessels.
3. The mixture is mixed well by pipetting the fluid back and forth.
4. 4 coated Mini tips, corresponding to the four assays, each aspirate 10 uL of the mixture, and the mixture is allowed to incubate with the capture protein on the surface for 5 minutes.
5. The mixture is discarded onto an absorbent waste pad located on the Cartridge, which ensures that the waste fluid is retained to prevent any possible contamination.
6. The 4 tips aspirate 11 uL of wash buffer, followed by a 1 minute incubation, after which the wash buffer is discarded onto the waste pad.
7. Step 7 is repeated 5 more times.
8. The 4 tips aspirate 10 uL of detection antibody, followed by a 5 minute incubation.
9. The fluid is discarded onto an absorbent pad, and the wash steps (steps 7 and 8) are repeated.
10. The four reaction tips aspirate 10 uL of ALP substrate from 4 sealed Round vessels containing substrate, followed by a 5 minute incubation.
11. The four tips are moved to the Luminometer Module where luminescence of each of the four tips is detected, and the corresponding count values transmitted to the LAS.

The count values are analyzed in the LAS, where a calibration function is applied, analysis is performed on these values and associated replicate, control, calibrator, QC, and outlier evaluation, and the final antibody concentrations are generated.

Performance Testing

For reference, the figures after FIG. 11 includes representative bench and clinical data has previously collected, along with template for system validation.

Performance Testing

In addition to the assembly-level and system-level tests which are done on every SPU that is manufactured, a set of SPUs will all undergo an extensive device validation exercise. The device validation exercise is meant to quantify the key performance metrics of the device (hardware and software internal to the device). An example of a device validation plan, detailing validation tests for selected modules (which are involved in the application discussed in this document) is attached (see document titled SPU validation template). The validation tests describe the metric to be tested, description of the test, number of replicates, and passing criteria for ensuring that the device.

By way of non-limiting example, the individual modules in the SPU go through tests to quantify precision, as well as hardware-level calibration. For instance, the luminometer is tested for precision in responding to a constant-intensity light source, and calibrated such that the same light source yields the same total counts across all Luminometer Modules. Similarly, the Fluorometer/Turbidimeter Module is characterized for temperature precision and accuracy. The Liquid Handling Module is independently characterized for volumetric precision, calibrated for accuracy, and re-tested for post-calibration bias. After assembly, there are system-level tests to ensure the device meets overall device accuracy.

Safety

For at least one embodiment of the SPU described herein, the SPU will comply with IEC 60601, IEC 62304, and ISO 14971 standards for Medical Devices. The electronics in the SPU have been designed to be in compliance with IEC standards.

Quality Control

For at least one embodiment of the SPU described herein, the SPU is designed and constructed for high accuracy and precision. Quality control ("QC") and calibration starts with individual modules in the device. All modules, including the Liquid Handling Module and detectors are independently qualified for precision, and independently calibrated for accuracy. This is followed by a complete system level QC check, which quantifies both accuracy and precision of the hardware. This approach is rather unique to The system, since most devices only go through an overall system level QC check and calibration.

For at least one embodiment of the SPU described herein, the SPU goes through several stages of QC checks to ensure high degree of accuracy and precision. As described above, the individual modules as well as the complete device is tested for accuracy and precision by running several QC protocols. Once installed in a Patient Service Center, the SPU also undergoes daily QC to ensure that the performance metrics are maintained within tight bounds. To facilitate this, PSCs have a stock of QC Cartridges. These Cartridges are associated with a QC protocol, which exercises the performance of various modules inside the SPU. The QC protocol yields raw detector data, which is transmitted to the LAS (similar to an actual sample run), where the detector data is analyzed and system performance metrics determined. This enables the LAS to exercise constant oversight on the SPUs, ensuring that any performance deficiency is immediately flagged, reported, and properly remedied by the CLIA-certified laboratory.

For at least one embodiment of the SPU described herein, the two assay methods also have on-board controls to ensure that the system performs adequately. For The Influenza NAA assays, the following on-board controls are run:

For at least one embodiment of the SPU described herein, sample collection and transfer control comprises: Each patient sample will carry varying amounts of human specific nucleic acid. For each sample processed, a control human RNaseP assay is run to verify appropriate sample collection.

For at least one embodiment of the SPU described herein, sample Prep control comprises: A non-natural/synthetic target in the form of DNA or RNA is spiked in the sample. This will be used as an internal calibrator to QC sample prep and amplification. This also checks the general performance of the chemistry and the device.

For at least one embodiment of the SPU described herein, No Template Control (NTC) comprises: For each assay, a NTC test will be run simultaneously to QC for background signal and contamination.

For the ELISA assays, there are positive control samples run simultaneously with the assay each time an assay is run (for each of the four assays). These four samples are processed in exactly the same way as the patient samples are processed (cf. ELISA protocol). The output from these control runs are used by the LAS to look for any performance deficiencies in the system in real time, thereby helping to ensure that the sample output is accurate.

Elements of Intended Use

In accordance with at least one embodiment described herein, in vitro diagnostic products ("IVDs") may include those reagents, instruments, and systems intended for use in diagnosis of disease or other conditions, including a determination of the state of health, in order to cure, mitigate, treat, or prevent disease or its sequelae. Such products are intended for use in the collection, preparation, and examination of specimens taken from the human body.

The system described in this non-limiting description is an IVD and is designed to be used in accordance with CLIA for CLIA-certified laboratory testing.

In one non-limiting example, all analysis will be done in CLIA-certified laboratory, applying intellectual property and associated technology in the LAS and SPU, and helping to minimize pre-analytic processing errors and variability in order to generate results of the highest quality.

Optionally, all tests are physician directed and reported back to ordering physicians directly through CLIA-certified laboratory. The SPU is intended to be used in PSCs.

For at least one embodiment of the SPU described herein, the SPU will be overseen by CLIA laboratory personnel in the PSC and CLIA-certified laboratory. Samples will be collected in the PSC by an appropriately certified phlebotomist or state licensed sample collection technician or nurse. The only actions for The PSC personnel to perform once the sample has been obtained are to place the sample into the Cartridge, press the touchscreen as prompted to open the SPU, place the Cartridge into the SPU, and press the touch screen as prompted to close the SPU and initiate processing. All sample preparatory steps are automated in the SPU and overseen by the LAS and CLIA-certified laboratory, and all analysis is done by the LAS in and overseen by CLIA-certified laboratory.

Elements of Intended Use for NAA:

For at least one embodiment of the SPU described herein, the influenza assays will identify and detect the following pathogens: Influenza A, Influenza A subtype H1, Influenza subtype 2009 H1, Influenza A subtype H3, Influenza subtype H5N1, Influenza subtype H7N9 and Influenza B to be measured alone or in combination or in combination with the Influenza ELISA assays below.

Optionally, the assays will be qualitative in nature.

For at least one embodiment of the SPU described herein, the assays are performed on samples collected in the form of nasopharyngeal swabs ("NPS"), nasopharyngeal aspirate ("NPA"), nasopharyngeal wash ("NPW"), or nasal swabs ("NS") processed by the SPU in PSCs, and analyzed by the LAS in CLIA-certified laboratory.

NPS, NPA, NPW or NS samples will be mixed automatically in the SPU. When placed into the SPU, the sample is automatically mixed by several cycles of pipetting to ensure maximal sample release from the swab so that no manual processing of the sample is required.

Optionally, Influenza testing is for prescription use.

For example, the test will be performed on individuals suspected of suffering from respiratory tract infections.

Optionally, the results will be reported as positive, equivocal, or negative for a given Influenza pathogen. This information can be for diagnosis of respiratory infection when used in conjunction with other clinical information. Positive results do not rule out co-infection with pathogens not tested on this panel. Negative results do not rule out respiratory infection and should not be used as the only basis for diagnosis or treatment.

Elements of Intended Use for ELISA:

For at least one embodiment of the SPU described herein, the influenza antibody panel will identify and detect IgG and IgM antibodies in plasma to the following pathogens: Influenza A and Influenza B to be measured alone or in combination or in combination with the Influenza NAA assays above.

Optionally, the assay will be qualitative in nature.

Optionally, the assays are performed on samples obtained from blood samples via traditional venipuncture or fingerstick, processed by the SPU in PSCs, and analyzed by the LAS in CLIA-certified laboratory.

By way of non-limiting example, the Influenza Ab testing is for prescription use.

Optionally, the test will be performed on individuals suspected of respiratory tract infection currently or previously.

Optionally, the test will be performed on individuals suspected of suffering from respiratory tract infections and may be used as a complementary tool for confirmation of diagnosis and to assess disease stage.

Optionally, the test will detect the presence of IgM antibodies directed at influenza A and B, positive results suggesting acute or recent infection.

Optionally, the test will detect the presence IgG antibodies directed at influenza A and B, positive results suggesting immunity from past exposure.

For at least one embodiment of the SPU described herein, the results will be reported as a negative, equivocal or positive based on cut-offs for measured antibody titers. A negative report confirms non-existence of any antibody in the patient sample. An equivocal report implies that presence or absence of the antibodies cannot be confirmed and repeat testing after 10-14 days may be recommended. A positive report definitively confirms the presence of antibodies and thus the diagnosis of a present or past infection with the said influenza strain. This information can be for diagnosis of respiratory infection when used in conjunction with other clinical information. Positive results do not rule out co-infection with pathogens not tested on this panel. Negative results do not rule out respiratory infection and should not be used as the only basis for diagnosis or treatment.

Description of how the Device is Planned to be Used in a Real-Life Setting

Real-Life Setting for NAA:

For at least one embodiment of the SPU described herein, these samples will be collected at a PSC from patients with a prescription for the relevant Influenza tests from their doctor. Samples will be collected in the PSC by an appropriately certified phlebotomist or state licensed sample collection technician or nurse using a nasopharyngeal swab, nasopharyngeal aspirate, nasopharyngeal wash, and nasal swab. The SPU performs sample preparatory steps and processing, during which it will extract and purify nucleic acid from the patient sample. The purified sample is then used in the NAA Influenza assay. The data will be analyzed by the LAS for pathogen detection and a report will be generated by CLIA-certified laboratory suggesting positive or negative identification of specific pathogens. This information will be made available to the ordering doctor directly for their diagnostic decision making.

Real-Life Setting for ELISA:

For at least one embodiment of the SPU described herein, these samples will be collected at a PSC from patients with a prescription for the relevant Influenza tests from their doctor. Samples will be collected in the PSC by an appropriately certified phlebotomist or state licensed sample collection technician or nurse via venous or fingerstick methods. The SPU performs sample preparatory steps and processing, during which it will prepare the blood sample for subsequent analysis. The prepared sample is used in a chemiluminescence based ELISA. The data will be analyzed by the LAS for influenza IgG and IgM titers and a report will be generated CLIA-certified laboratory suggesting positive, equivocal or negative levels of the four antibodies. This information will be made available to the ordering doctor directly for their diagnostic decision making.

Risk Analysis

Results obtained from these tests can be used for diagnosis of respiratory infection when used in conjunction with other clinical information. Positive results do not rule out co-infection with pathogens not tested on this panel. Negative results do not rule out respiratory infection and should not be used as the only basis for diagnosis or treatment. As the presence of antibodies is not associated with signs or symptoms, an incorrect serologic result could falsely suggest that a patient has protective IgG antibodies directed at influenza strains. Additional patient risk factors such as the patient age and medical history should be considered for the basis of treatment.

NAA Proposed Study Design(s) and Analytical and Pre-Clinical Performance

For at least one embodiment of the SPU described herein, method characterization comprises: Basic analytical performance of the method in terms of limit of detection, specificity, carry-over, interference, and inclusivity/exclusivity will be established in this phase.

For at least one embodiment of the SPU described herein, determination of amplification cut-offs comprises: This phase will comprise of a pre-clinical study, where samples will be analyzed to establish infection time cutoffs. In combination with the precision of the method itself, these data will be used to establish cut-offs for negative and positive classification. Precision of the method at points near the cut-offs will then be established.

For at least one embodiment of the SPU described herein, method comparison comprises: The final phase of pre-clinical demonstrations will compare The method as characterized in (1) and (2) above with a reference method and diagnosis.

The study design comprises of the following:
Sensitivity and Limit of Detection (LOD)
Specificity
Carryover study
Interference substances
Inclusivity/Exclusivity
Determination of cut-off criteria
Reproducibility (precision)
Further details on each of the above categories:
Sensitivity and Limit of Detection (LOD)

Optionally, the purpose of this study is to determine the limit of detection (LOD) for The NAA assay. The LOD95 is the viral titer at which >95% of known positive samples test positive using the NAA assay.

One non-limiting example comprises making serial 10-fold dilutions of each virus from $10^6$ to $10^1$ organisms, or serial 10-fold dilutions ranging from 1000 TCID50, to 10 TCID50.

One non-limiting example may involve performing each assay 20 times for each virus and for each dilution, and record positives and negatives.

|  | 1000 TCID$_{50}$ | 100 TCID$_{50}$ | 10 TCID$_{50}$ |
| --- | --- | --- | --- |
| Influenza H1N1 | #Pos: #Neg: | #Pos: #Neg: | #Pos: #Neg: |
| Influenza H1N1 (2009) | #Pos: #Neg: | #Pos: #Neg: | #Pos: #Neg: |
| Influenza H3N2 | #Pos: #Neg: | #Pos: #Neg: | #Pos: #Neg: |
| Influenza B | #Pos: #Neg: | #Pos: #Neg: | #Pos: #Neg: |
| Influenza A | #Pos: #Neg: | #Pos: #Neg: | #Pos: #Neg: |
| Influenza H5N1 | #Pos: #Neg: | #Pos: #Neg: | #Pos: #Neg: |
| Influenza H7 | #Pos: #Neg: | #Pos: #Neg: | #Pos: #Neg: |
| Influenza N9 | #Pos: #Neg: | #Pos: #Neg: | #Pos: #Neg: |

Acceptance Criteria:

If 1 or fewer known positive samples scores as negative then the LOD95 has been confirmed for that titer.

If >1 known positive samples scores as negative then the LOD95 has been rejected for that titer.

Specificity

Test the lysates from clinical samples spiked with nucleic acid from (a) metapneumovirus, (b) parainfluenzavirus 1, (c) parainfluenza virus 3, and (d) RSV. The nucleic acid concentration should reflect expected median viral loads in clinical specimens.

Repeat the above LOD procedure with NA samples spiked with nucleic acid from (a) metapneumovirus, (b) parainfluenzavirus 1, (c) parainfluenza virus 3, and (d) RSV. Calculate new LOD in mixed specimens.

Carryover

Set up a plate with Pathogen count as follows:

| NAA test | H1N1 | H1N1 (2009) | H3N2 | Influenza B | Influenza A | Influenza H5N1 | Influenza H7 | Influenza N9 |
|---|---|---|---|---|---|---|---|---|
| Viral titer | 1.00E+050 | 1.00E+050 | 1.00E+050 | 1.00E+050 | 1.00E+050 | 1.00E+050 | 1.00E+050 | 1.00E+050 |
| | 1.00E+050 | 1.00E+050 | 1.00E+050 | 1.00E+050 | 1.00E+050 | 1.00E+050 | 1.00E+050 | 1.00E+050 |
| | 1.00E+020 | 1.00E+020 | 1.00E+020 | 1.00E+020 | 1.00E+020 | 1.00E+020 | 1.00E+020 | 1.00E+020 |
| | 1.00E+020 | 1.00E+020 | 1.00E+020 | 1.00E+020 | 1.00E+020 | 1.00E+020 | 1.00E+020 | 1.00E+020 |
| | 0 | 0 | 0 | 0 | 0 | 0 | 0 | 0 |
| | 0 | 0 | 0 | 0 | 0 | 0 | 0 | 0 |
| | +control | +control | +control | +control | +control | +control | +control | +control |

Acceptance Criteria:

Compare relative time to detection or relative cycle number at which signal crosses threshold (CT) in zero wells that are adjacent to 1.00E+05 and 1.00E+02 wells versus 0 wells adjacent to other 0 wells.

NAA assay run in negative wells exceeds maximum number of cycles or cycle time for the assay.

Interfering Substances

Performance of the NAA assay in the presence of interfering substances has been evaluated.

The following interfering substances have been tested:

| Endogenous Substances: | Competitive Interfering Microorganisms: | Exogenous Substances: | Laboratory Reagents: |
|---|---|---|---|
| Human Blood (with Na Citrate) | Respiratory Syncytial Virus A | Bactroban nasal | Bleach (1%, 2%/15, % v/v) |
| Mucin (bovine submaxillary gland) | Human Rhinovirus | Flonase | Disinfecting wipes |
| Human Genomic DNA | Influenza A2009 HINI | Nasonex | Ethanol (7% v/v) |
| | Staphylococcus aureus | Astelin | DNAzap (I % v/v) |
| | Nleisseria meningitis | Anefrin Nasal Spray | RNaseOut (I % v/v) |
| | Corynebacterium diphtheria | NeoSynephrine Vicks VapoRub cough suppressant ZiCam Allergy Relief Nasal Gel UTM | |

Acceptance Criteria:

Mean time to detection of triplicates for positives without interfering substances shall not be different from mean time to detection of positives in the presence of interfering substances using the student's T-test.

Inclusivity/Exclusivity

The following tables summarize the inclusivity and exclusivity pathogens to be evaluated for each of the four Influenza assays.

| | Influenza A | | |
|---|---|---|---|
| Inclusivity | | Exclusivity | Cross reactivity |
| A/California/7/2009 (H1N1 novel) A/Solomon lslands/3/2006 (H1N1) A/Malaya/302/54 (H1N1) A2/Aichi2/68 (H3N2) A/Victoria/3/75 (H3N2) A/Hong Kong/33982/2009(H9N2) A/Egypt/N03072/2010(H5N1) A/Turkey/Turkey/1/2005xPR8 (H5N1) | | B/Maryland/1/59 B/Russia/69 | Adenovirus Candida albicans Klebsiella pneumonia E. coli 5 ng hgDNA Bordetella pertussis A/WS/33 (H1N1) B/Hubei-Wujiagang/158/2009 Pseudomonas aeruginosa Staphylococcus aureus Streptococcus pyogenes |

| Influenza A/H1 | | |
|---|---|---|
| Inclusivity | Exclusivity | Cross reactivity |
| A/New Caledonia/20/1999 | B/Lee/40 | Adenovirus |
| A/PR/8/34 | A/California/7/2009 (H1N1) | Candida albicans |
| A/FM/1/47 | A/Port Chalmers/1/73 | Klebsiella pneumonia |
| A/WSN/33 | | *E. coli* |
| A1/Denver/1/57 | | 5 ng hgDNA |
| | | Bordetella pertussis |
| | | A/WS/33 (H1N1) |
| | | B/Hubei-Wujiagang/158/2009 |
| | | Pseudomonas aeruginosa |
| | | *Staphylococcus aureus* |
| | | *Streptococcus pyogenes* |

15

| Influenza A/H1 2009 | | |
|---|---|---|
| Inclusivity | Exclusivity | Cross reactivity |
| A/California/7/2009) | Flu A/Solomon lslands/3/2006 | Adenovirus |
| | A/FM/1/47 | Candida albicans |
| | A2/Wisconsin/67/2005 | Klebsiella pneumonia |
| | A/Hong Kong/8/68 | *E. coli* |
| | B/Brisbane/60/2008 | 5 ng hgDNA |
| | B/Russia/69 | Bordetella pertussis |
| | A/Hong Kong/33982/2009 | A/WS/33 (H1N1) |
| | A/Egypt/N03072/2010 | B/Hubei-Wujiagang/158/2009 |
| | A/turkey/Turkey/1/2005 | Pseudomonas aeruginosa |
| | | *Staphylococcus aureus* |
| | | *Streptococcus pyogenes* |

| Influenza A/H3N2 | | |
|---|---|---|
| Inclusivity | Exclusivity | Cross reactivity |
| A/Wisconsin/67/2005 (H3N2) | A/California/7/2009 | Adenovirus |
| A/Port Chalmers/1/1973 (H3N2) | A/Solomon lslands/3/2006 | Candida albicans |
| A/Hong Kong/68 (H3N2) | A/FM/1/47 | Klebsiella pneumonia |
| A/Aichi/2/1968 (H3N2) | B/Brisbane/60/2008 | *E. coli* |
| A/Victoria/3/1975 (H3N2) | B/Russia/69 | 5 ng hgDNA |
| A2/Wisconsin/67/2005 | A/Hong Kong/33982/2009 | Bordetella pertussis |
| A/Hong Kong/8/68 | A/Egypt/N03072/2010 | A/WS/33 (H1N1) |
| | A/turkey/Turkey/1/2005 | B/Hubei-Wujiagang/158/2009 |
| | | Pseudomonas aeruginosa |
| | | *Staphylococcus aureus* |
| | | *Streptococcus pyogenes* |

| Influenza B | | |
|---|---|---|
| Inclusivity | Exclusivity | Cross reactivity |
| B/Wisconsin/1/2010 | A/California/7/2009 (H1N1 pdm09) | Adenovirus |
| B/Florida/07/04 | A/Solomon lslands/3/2006 (H1N1) | Candida albicans |
| B/Hubei-Wujiagang/158/2009 | A/FM/1/47 (H1N1) | Klebsiella pneumonia |
| B/Brisbane/60/2008 | A2/Wisconsin/67/2005 (H3N2) | *E. coli* |
| B/Panama/45/90 | A/Hong Kong/8/68 (H3N2) | 5 ng hgDNA |
| B/Victoria/504/00 | A/Hong Kong/33982/2009(H9N2) | Bordetella pertussis |

Influenza B

| Inclusivity | Exclusivity | Cross reactivity |
|---|---|---|
| B/Maryland/1/59 | A/Egypt/N03072/2010(H5N1) | A/WS/33 (H1N1) |
| B/R75 | A/turkey/Turkey/1/2005 (H5N1) | B/Hubei-Wujiagang/158/2009 |
| B/Mass/3/66 | | Pseudomonas aeruginosa |
| B/Lee/40 | | *Staphylococcus aureus* |
| B/Russia/69 | | *Streptococcus pyogenes* |

Influenza H5N1

| Inclusivity | Exclusivity | Cross reactivity |
|---|---|---|
| A/Egypt/N03072/2010(H5N1) | A/California/7/2009 (H1N1 novel) | Adenovirus |
| A/India/NIV/2006(H5N1) | A1/Denver/1/57 (H1N1) | Candida albicans |
| NIBRG-23 A/Turkey/1/2005 (H5N1) | A/FM/1/47 (H1N1) | Klebsiella pneumonia |
| | A2/Aichi2/68 (H3N2) | E. coli |
| | A/Victoria/3/75 (H3N2) | 5 ng hgDNA |
| | A/Hong Kong/33982/2009(H9N2) | Bordetella pertussis |
| | B/Malaysia/2506/2004 | A/WS/33 (H1N1) |
| | B/Russia/69 | B/Hubei-Wujiagang/158/2009 |
| | | Pseudomonas aeruginosa |
| | | *Staphylococcus aureus* |
| | | *Streptococcus pyogenes* |

Influenza H7

| Inclusivity | Exclusivity | Cross reactivity |
|---|---|---|
| | A/California/7/2009 (H1N1 novel) | Adenovirus |
| | A1/Denver/1/57 (H1N1) | Candida albicans |
| | A/FM/1/47 (H1N1) | Coronavirus |
| | A2/Aichi2/68 (H3N2) | E. coli |
| | A/Victoria/3/75 (H3N2) | hgDNA |
| | A/Hong Kong/33982/2009(H9N2) | Rhinovirus |
| | B/Malaysia/2506/2004 | Influenza A |
| | B/Russia/69 | Influenza B |
| | | Pseudomonas aeruginosa |
| | | *Staphylococcus aureus* |
| | | *Streptococcus pyogenes* |

Influenza N9

| Inclusivity | Exclusivity | Cross reactivity |
|---|---|---|
| | A/California/7/2009 (H1N1 novel) | Adenovirus |
| | A1/Denver/1/57 (H1N1) | Candida albicans |
| | A/FM/1/47 (H1N1) | Coronavirus |
| | A2/Aichi2/68 (H3N2) | E. coli |
| | A/Victoria/3/75 (H3N2) | hgDNA |
| | A/Hong Kong/33982/2009(H9N2) | Rhinovirus |
| | B/Malaysia/2506/2004 | Influenza A |
| | B/Russia/69 | Influenza B |
| | | Pseudomonas aeruginosa |
| | | *Staphylococcus aureus* |
| | | *Streptococcus pyogenes* |

In one embodiment, mean time to detection of negatives shall be at minimum 10 minutes greater than the mean time to detection of positives.

Optionally, all 3 replicates obey the above criteria.

In one embodiment, mean time to detection of negatives statistically different from mean time to positives using the students T-test.

Acceptance Criteria: Inclusivity

For the pan-Influenza A test, a mean range of time to detection will be assessed across all Influenza A substrains, which shall not exceed 5 minutes.

For each pan-Influenza A test on a given Influenza A substrain, mean time to detection shall be statistically different from the mean time to detection of a pan-Influenza A test on a negative control.

For Influenza subtype specific assay, mean time to detection shall be statistically different from the mean time to detection of the Influenza subtype specific assay of the negative control.

The % CV for time to detection of all positives and negatives shall be <15%.

Determination of Assay Cutoffs

For at least one embodiment of the SPU described herein, the isothermal amplification process generates fluorescence upon incorporation of the double-stranded-DNA intercalating dye, and the relative fluorescence units (RFUs) measured once per minute over a 30 minute reaction. An amplification signal is detected if a statistical changepoint is found, with two populations of measurements, the latter of which has a mean RFU at least 1.5 times greater than the population of earlier measurements. The changepoint, the measurement that divides the samples into two populations, is used then to interpolate the time at which the amplification curve of the observed RFUs exceed the mean of the first population of measurements.

For at least one embodiment of the SPU described herein, cut-off times for making positive/equivocal/negative calls will be determined for each target empirically. A set of experiments for each target, repeated over five days, will be conducted that included 8 replicates each of three dilutions (LoD, 10×LoD, and 100×LoD), as well as 8 NTCs, using the target primers for amplification. These data will be processed using a receiver-operator character (ROC) analysis as per CLSI guidance document MM3-A2 and EP24-A2. The best threshold detection time for distinguishing positives and negatives determined using the Youden test statistic as implemented by the R package, pROC.

Reproducibility (Precision)
  Precision: Mean Time to Detection (Cycles or Minutes)
    Evaluate relative time to detection ($\Delta T$) for each pathogen at 0, $1\times10^2$, $1\times10^4$ and $1\times10^6$ copies or 10 $TCID_{50}$, 10 $TCID_{50}$, 100 $TCID_{50}$, 1000 $TCID_{50}$
    $\Delta T$ is defined as the time to detection of a zero template reaction minus the time to detection of a reaction containing target nucleic acid.
    Continue over 5 days to obtain 20 data points.
    Calculate $\Delta T$ mean, SD and % CV.$\Delta$
    Acceptance criteria: $\Delta T$ CV<20%
  Precision: % positive, equivocal and negative at 3 detection limits
    Prepare nucleic acid from high negative (LOD/10), low-positive (LOD) and high positive (3×LOD)
    Perform the above 4 times and record positive, negative and equivocal results, as well as mean relative time to detection for each.
    Continue over 5 days to obtain 20 data points.
    Calculate $\Delta T$ mean, SD and % CV.
    Acceptance criteria:
    LOD/10: $\Delta T$ CV<20%
    LOD $\Delta T$ CV<15%
    3×LOD $\Delta T$ CV<15%

Method Comparison

In one non-limiting example, a method of comparison is provided to estimate the sensitivity, specificity, PPV and NPV of the NAA assay using Filmarray as the comparator (device). Additionally CDC Human Influenza Virus Real-Time RT-PCR Diagnostic Panel & CDC Human Influenza Virus Real-Time RT-PCR Diagnostic Panel-Influenza A/H7 (Eurasian Lineage) Assay On ABI 7500 Fast Dx Real-Time PCR instrument will be used as method for H5N1 and H7N9 assay.

Optionally, for each clinical sample, each test will be run in duplicate, except for the NTC, which will be run for each primer pair. In total, 30 amplification reactions will be measured. A positive determination is made for a sample when amplified products are detected prior to the assay cutoff time in both templated replicates, if the later of the two is no more than 20% later. For all but the Influenza B assay, there is an additional layer of internal validation, namely both the pan-Influenza A and the specific subtype (a total of four wells) should be detected before a positive determination is made, and the coefficient of variance (CV) between replicates of each of the two tests is <20%. A run with no positive calls for any of the influenzas is only valid if both the RnaseP and spike-in controls are positive by these metrics.

Optionally, the following will invalidate a run and could necessitate retesting:
  Detection of product in any of the NTC wells when a positive call is made for that target
  Negative results for any of the pathogens, along with negative results in the Rnase P and spike-in controls
  A negative result in the spike-in control, regardless of other results (indicates lack of template, so observed products are likely non-templated)
  A positive result for a pathogen along with a negative result for Rnase P is still valid, as a high level infection could overcome poor sample collection.

Run samples each day using NAA and Filmarray RP/RT-PCR methods over 20 days using retrospective samples from demographically diverse population covering gender and age:

| Target | Positive | Negative |
|---|---|---|
| Influenza H3N2 | 50 | 100 |
| Influenza H1N1 | 50 | 100 |
| Influenza H1N19 | 50 | 100 |
| Influenza B | 50 | 100 |
| Influenza A | 50 | 100 |
| Influenza H5N1 | | |
| Influenza H7 | | |
| Influenza N9 | | |

One non-limiting example may involve carefully documentomg positives and negatives for each pathogen on each method.

Optionally, the method may include calculating the sensitivity, specificity, PPV and NPV of the NAA assay and a control assay such as a Filmarray assays.

Optionally, the method may include calculating the percent concordance and percent discordance of NAA versus Filmarray assay and CDC approved RT-PCR assays.

Acceptance Criteria: Concordance>95%, Sensitivity>90%, Specificity>95%, PPV>80%, NPV>80%.

Note: Avian influenzas (H5N1 and H7N9) is currently extremely rare in the U.S. Because of this rare incidence, the interpretation and reporting of results for testing in the U.S. for H5N1 and H7N9 will incorporate the following logic to limit the impact of minor type 1 errors rates. Namely, the H5, H7, and N9 results will not be reported unless the influenza A test is positive and the three tested A subtypes (H1 seasonal, H1 2009, H3N2) are all negative. Alternate reporting logic is implemented when testing is performed in a region with high incidence of avian influenza and/or if the ordering physician indicates high likelihood of avian influenza infection in the subject when ordering the test. In this latter situation, results will be reported for H5N1 and H7N9 irrespective of results for the three influenza A subtypes for that sample.

ELISA Proposed Study Design(s) and Analytical and Pre-Clinical Performance

For at least one embodiment of the SPU described herein, the following may apply:

In one non-limiting example, analytical performance will again be evaluated in accordance with CLSI and FDA guidelines. The study is divided into three major phases:

Method characterization: Basic analytical performance of the method in terms of precision, specificity, limit of detection and other metrics will be established in this phase.

Determination of analyte concentration cut-offs: This phase will comprise of a pre-clinical study, where samples from known positive and known negative patients will be analyzed to establish ranges of antibody titer for these patients as measured with this method. In combination with the precision of the method itself, these data will be used to establish cut-offs for negative-equivocal and equivocal-positive classification. Precision of the method at points near the cut-offs will then be established.

Method comparison: The final phase of pre-clinical demonstrations will compare The method as characterized in (1) and (2) above with a reference method and diagnosis.

Method Characterization:

For at least one embodiment of the SPU described herein, the following may apply:

For at least one embodiment of the SPU described herein, specimen information comprises: Studies conducted to determine recommended methods for collection and storage of specimens. The proposed specimens to be used for these assays are venous blood and fingerstick blood.

Development of negative and positive controls: Stabilized controls that are contrived to always have a negative result or a positive result will be developed. The stability of these controls and the results generated with them will be demonstrated over the time that these controls are desired to be valid. Expiration dates for control lots can then be assigned during manufacturing, thus maintaining strict quality. During the proposed study, controls will be run as part of each experiment.

Precision: Precision (reproducibility or repeatability) of the method will be characterized at three different concentration levels spanning the analytical range. At each level, 31 replicates of a contrived sample in plasma will be analyzed. The precision at each level will be reported as % CV. Further, in accordance with CLSI guidance document EP05-A2, precision will be characterized over at least 10 days and at least 100 runs. Within-run, across-run and between-day precision will also be characterized as % CV.

Limit of detection: CLSI guidance document EP17-A2 details the procedure appropriate for establishing the limit of blank and limit of detection. Briefly, a value which is desired to be claimed as the limit of detection is selected and the standard deviation of the measurement at this value is determined using multiple replicates of a contrived sample. Using a similarly established limit of blank and the standard deviation of low samples, the limit of detection can be established.

Accuracy: For the purposes of method characterization, accuracy will be determined as the comparability of assay measurement with a measurement of the same sample. It is pointed out here that the final nature of the assays are semi-quantitative (qualitative). However, during the method characterization phase, the assays are treated like a quantitative assay and the result is antibody titer. The comparability of this titer will be established using one or more of the kits available commercially (ARP, IBL etc.). Accuracy will be reported as the correlation coefficient and bias of method with. At least 40 samples spanning the negative to mid-to-high positive range will be analyzed for this demonstration.

Analytical specificity: Cross-reactivity: Clinical symptoms of influenza are typical (it has been called an "unchanging disease due to a changing agent"); therefore absence of cross-reactivity is critical in an assay that serves to confirm the diagnosis of influenza infection. As part of method characterization, absence of cross-reactivity will be demonstrated with antibodies against organisms that may cause flu-like symptoms, such as parainfluenza, herpes, hepatitis C, Lyme disease, rabies, myocarditis, Q fever, dengue fever and poliomyelitis. Samples that are confirmed to be negative for influenza A antibodies and influenza B antibodies will be spiked with antibodies against the above pathogens and analyzed for InfA IgG/IgM and InfB IgG/IgM.

Analytical specificity: Interference: Interference by bilirubin, hemoglobin, icterus and lipemia will be evaluated and rejection criteria for each of the above will be documented.

Matrix comparison: The matrices to be used in these assays are whole blood samples from venipuncture and fingersticks and the plasma and serum derived from them. All matrices will be tested in terms of clinical and spiked samples. Correlation and bias for each pair will be calculated and documented. These measures will be used to transfer reference ranges in subsequent studies if required.

For at least one embodiment of the SPU described herein, high dose hook effect comprises (artifactually low absorbance measurements at high antigen concentration): measurements taken to confirm the existence or extent of high dose hook effect, if any. The impact of the high dose hook, if any, will be investigated by experiments using antigen concentration titrations.

Reagent and sample stability studies: Reagent stability will be demonstrated over a period that is desired to be claimed as the life of a Cartridge. Precision and accuracy will be verified by performing at least 12 measurements of 3 levels of analyte over the time period. The acceptable level of deterioration in precision and accuracy will be evaluated in the context of classification and reporting of results. Similarly, samples will be stored as whole blood, plasma, and serum at room temperature, 4° C. and −20° C. for different time periods ranging from a few hours to several days. Precision and accuracy of the measurement for these samples will be characterized and documented.

Determination of Analyte Concentration Cut-Offs:

For at least one embodiment of the SPU described herein, the following may apply:

Determination of desired cut-off analyte concentrations: The ELISA assays will generate results in three categories for each of the 4 antibodies: negative, equivocal and positive. Therefore there are two cut-off values that need to be established. These cut-offs will be established as part of a pre-clinical study.

Testing methodology may include using paired NPS, NPA, NPW, and NS and fingerstick and venous samples will be collected from at least 100 healthy individuals before the onset of the US influenza season. The NPS, NPA, NPW, or NS will be analyzed to confirm the absence of any viral load. The blood samples will be analyzed using an antibody detection method to confirm the absence of any influenza A/B antibodies. Measurements of antibody titers on these samples using The method will serve to establish the negative population titers—the baseline.

Testing methodology may include using paired NPS, NPA, NPW, and NS and fingerstick and venous samples will be collected from at least 100 symptomatic individuals during the US influenza season. The NPS, NPA, NPW, or NS will be analyzed to confirm the presence of detectable viral load. The blood samples will be analyzed using an antibody detection method to confirm the presence of influenza A/B antibodies. Measurements of antibody titers on these samples using The method will serve to establish the positive population titers.

Based on distribution of antibody titers in the negative population and the positive population, and the precision of the assay at or near those titer values (as characterized in Section A above), the negative-equivocal and equivocal-positive cut-offs can be established. The cut-offs will be defined as levels where there is a 50% chance of returning either result around it.

After defining the cut-offs, precision at the cut-off levels will be determined using contrived samples and at least 31 replicates.

Method Comparison and:

For at least one embodiment of the SPU described herein, the following may apply:

It should be understood that, typically, kits for Influenza antibody measurements that appear to be available commercially are not for CLIA-certified laboratory testing but rather appear to be waived kits for IgG. ARUP, a reference laboratory, will therefore be used as for the ELISA assays.

At least 150 positive samples are obtained and split, stored appropriately, and shipped to a reference laboratory to obtain values. Classification of each sample as negative, equivocal or positive will be compared in the form of a truth table (e.g. shown below).

| → | Negative | Equivocal | Positive |
|---|---|---|---|
| ↓ | | | |
| Negative | | | |
| Equivocal | | | |
| Positive | | | |

Each discrepant classification will be investigated and resolved. At the end of the process, for acceptance, at least 95% of the points should show concordance.

Specimen Information

Specimen Information for NAA:

For at least one embodiment of the SPU described herein, the following may apply:

The NAA assays are performed on samples collected in the form of nasopharyngeal swabs ("NPS"), nasopharyngeal aspirate ("NPA"), nasopharyngeal wash ("NPW"), or nasal swabs ("NS") from individuals suspected of suffering from a respiratory infection. To collect a sample from an NPS that has been applied to a subject's nasal passage, the NPS is placed inside a Swab vessel embedded in the Cartridge which is pre-filled with a transfer medium. The swab handle may be broken-off, and the vessel capped to preserve sample integrity. Most of the sample on the swab is released on contact into the transfer medium. When processed, the sample is automatically mixed by several cycles of pipetting to ensure maximal sample release from the swab so no human processing is required. Samples will typically be processed and analyzed within several hours of their acquisition; thus, fresh samples will typically be used. However, sample stability is tested by maintenance of test samples for various times under typical storage conditions. During transport, the samples are stored in Universal transport media (UTM) which is formulated for maximum sample stability and pathogen viability. Furthermore, samples are transported in a frozen state (on dry ice) to further increase stability.

Specimen Information for ELISA:

For at least one embodiment of the SPU described herein, the following may apply:

Whole blood, serum, or plasma may be used for ELISA assays. In most cases, whole blood collected by fingerstick or venipuncture will be used for ELISA testing. Such samples will typically be processed and analyzed within several hours of their collection; thus, the samples used will be fresh samples. However, sample stability is tested by maintenance of test samples for various times under typical storage conditions. During transport, the whole blood samples will be stored in vessels or Nanotainer tubes, as applicable, and stored at 4° C. with either heparin or EDTA anti-coagulant. Assays can be performed on whole blood, plasma or serum samples.

Comparison to the Subject Device

See the "Performance Testing/Product Development—Performance Testing" Section for more information regarding information about one non-limiting example of the system, including the SPU and any assays it may be configured to run.

NAA:

| Element | SPU |
|---|---|
| Organisms Detected | Influenza A, Influenza A/H1, Influenza A/H3, Influenza A/H1-2009, Influenza B |
| Analyte | RNA or DNA |
| Technological Principles | Multiplex Nucleic Acid |
| Specimen Types | Nasopharyngeal swabs, nasopharyngeal aspirate, and nasopharyngeal wash |
| Test Interpretation | Automated test interpretation and report generation. User cannot access raw data |
| Additional Organisms Detected | H5N1 and N7N9 subtypes |
| Technological Principles | Recombination based isothermal method (See the "Device Description - Nucleic Acid Amplification (NAA) Assay for Influenza Detection - NAA Principle" Section for more information) |
| Specimen Type | Nasal swab |
| Instrumentation | SPU |
| Test to result | <40 mins |
| Sample Preparation Method | Sample processing is automated in SPU |
| Additionally | ELISAs can be performed simultaneously |
| Reagent Storage | Reagents stored at 4° C. |
| User Complexity | Low |

| Element | NAA |
|---|---|
| Organisms Detected | Influenza A, Influenza A/H1, Influenza A/H3, Influenza A/H5 (Asian lineage), Influenza A/H1pdm09, Influenza B and Influenza A/H7 (Eurasian Lineage) |
| Analyte | RNA or DNA |
| Technological Principles | Multiplex Nucleic Acid, see below for difference |
| Specimen Types | Nasopharyngeal swabs, nasopharyngeal aspirate, and nasopharyngeal wash |
| Organisms Detected | For H7N9, H7 and N9 (two separate genes) are detected for further accuracy. |
| Technological Principles | Recombination based isothermal method (more info in Principle section) |
| Instrumentation | Device |
| Test to result | 45 mins |
| Sample Preparation Method | Sample processing is automated in instrument. |
| Additionally | ELISA can be performed simultaneously |
| Reagent Storage | Reagents stored at 4° C. |
| User Complexity | Low |
| Test Interpretation | Automated test interpretation and report generation. User cannot access raw data. |

ELISA:

It should be understood that typically regulatory approved kits for Influenza antibody measurements that appear to be available commercially are not for CLIA-certified laboratory testing but rather appear to be waived kits for IgG. ARUP, a reference laboratory, will therefore be used as for the ELISA assays.

At least 150 positive samples are obtained and split, stored appropriately, and shipped to a reference laboratory to obtain values. Classification of each sample as negative, equivocal or positive will be compared in the form of a truth table (e.g. shown below).

| → | Negative | Equivocal | Positive |
|---|---|---|---|
| ↓ | | | |
| Negative | | | |
| Equivocal | | | |
| Positive | | | |

Each discrepant classification will be investigated and resolved. At the end of the process, for acceptance, at least 95% of the points should show concordance.

Clinical Performance and Study Design Elements
Prospective Clinical Study

The primary goal of this prospective study is to supplement existing clinical data to characterize the accuracy of the influenza assays run on The SPU and LAS for the diagnosis of influenza A and influenza B infections in patients suspected of influenza infections. Combining highly sensitive NAA tests with serologic measures is believed to have several advantages over traditional methods as detailed below.

The traditional influenza testing approach includes rapid testing methods, followed in some cases by confirmatory testing (e.g., RT-PCR or culture). The problem with this approach is that rapid test methods generally have poor accuracy. Product insert information and research publications indicate that rapid testing only achieves sensitivities of 50-70% and specificities of 90-95%. This can yield a very high frequency of false negatives. Confirmatory testing is traditionally expensive with slow turnaround times, leading to delays in treatment and possibly inappropriate treatment. Moreover, rapid test methods do not distinguish between influenza A subtypes. Such viral subtyping can be critical for risk assessment, treatment, vaccine planning, and surveillance.

The SPU and LAS enables one to easily and rapidly perform both highly sensitive and specific NAA tests as well as serological testing. This approach yields both very high accuracy (sensitivity and specificity) and also provides information concerning the stage of the infection and state of the immune response. This timely and rich information can facilitate medical care, such as the decision to treat with an antiviral medication or not. It can also facilitate assessment of infectivity. Simultaneous testing in two modalities, namely gene-based NAA testing and immune/serologic testing, provides two orthogonal tests which should enhance overall performance. For example, early infections may be detected by NAA methods but not by serologic tests. Conversely, poor recovery of mucus or low viral loads in the upper respiratory tract and nasal cavity could result in false negative results by nasopharyngeal testing alone, while blood-based serologic testing may still reveal a positive result.

Influenza strains are well known for antigenic variation. Antigenic variation is classified into two types: antigenic drift that results in changes in few amino acids and antigenic shift which is the outcome of acquiring new structural proteins. Such variations can lead to the rapid spread of new viruses, more severe disease, as well as poor diagnostic test performance. The influenza panel is designed to be more tolerant to antigenic variation. Namely, the use of primers directed at both highly conserved genes as well as more selective genes provides both robustness to antigenic variations as well as enhanced specificity. In addition, serologic testing can help improve test performance in the face of antigenic drift.

The SPU and LAS enable CLIA oversight of sample processing with subsequent analysis in and under the oversight of The CLIA laboratory. This approach has clear advantages compared to traditional error-prone practices that include manual sample preparation with minimal oversight and shipping of samples to laboratories for analysis.

Nasopharyngeal aspirates or nasal wash specimens are commonly used for the detection of respiratory viruses. However these procedures are generally unpleasant. Obtaining an aspirate requires a suction device, a feature which make it unfeasible for widespread use in clinical practice. Less invasive testing with nasal swabs, which will be evaluated in this study alone, in comparison to aspirates and wash specimens, and in combination with blood samples, should enable increased patient participation and help improve overall healthcare response and surveillance.

Study Plan:

The clinical performance of The SPU will be evaluated in a prospective study. Nasopharyngeal swab, nasopharyngeal aspirate, nasopharyngeal wash, or nasal swab samples and simultaneous whole blood samples will be collected from subjects exhibiting flu-like symptoms at 3 U.S. sites during the 2013/2014 respiratory season. The samples will be collected by trained technicians and processed using The SPU at Patient Service Center ("PSC"). Each site will have 4 SPU's. Analysis will be done through the LAS. Testing accuracy and performance will be determined by comparison to comparable methods, including traditional CLIA-certified laboratory processing and analysis.

Clinical study sites are selected based on the desired geographic/demographic variation of the potential subject populations. Subjects will be selected from diverse demographic groups. Each site will enroll 334 patients, for a total of 1,002 subjects. Subjects will be screened for exhibiting signs and symptoms of respiratory infection including but not limited to fever, cough, sore throat, runny/stuffy nose, myalgia, earache, headache, chills, or fatigue. The subjects may or may not have had respiratory infection testing ordered by a physician. Written informed consent will be obtained from each subject and/or their parent/guardian (if under 18) at the time of enrollment into the study. To de-identify specimens, each subject will be assigned a Volunteer Identification Number (VIN) to track the sample. At the time of enrollment the following information will be recorded on the Case Report Form (CRF): 1) age; 2) sex; 3) information about their suspected respiratory infection, i.e., signs and symptoms, date of onset; and 3) current medications (self-reported and/or collected from medical records).

Technicians at the PSC will be trained on both the sample collection process as well as the basic operations of The SPU according to the intended use and associated instructions for use.

Three sample types (nasopharyngeal swab, nasopharyngeal aspirate, or nasopharyngeal wash) will be collected across 900 of the subjects. One sample type will be collected per subject and two swabs will be collected from each subject (one from each nostril). One swab will be used for testing on The System, and the second swab will be used for testing on the method (Idaho Tech, Biofire and CDC RT-PCR kits for Flu panel). Two nasal swabs (again one from each nostril) will be collected from the remaining 102 patients and run on both The System and the CDC RT-PRC kits for Flu panel. In addition, two whole blood samples from each patient will be collected for testing on The platform as well as the method (reference method performed at ARUP, a reference laboratory). A small sample collected from the fingerstick will be used for processing on The SPU, while a venous draw will be used for the method. Any conflicting results will be further investigated by viral culture and sequencing.

Statistical Analysis Plan for Clinical Performance Study

The main outcome of this study will be the determination of the diagnostic accuracy of the SPU influenza assays. To this end, concordance, sensitivity, specificity, positive predictive value ("PPV"), and negative predictive values ("NPV") will be calculated including 95% confidence intervals (CLSI guidance document EP12-A2).

These performance metrics will be calculated across all sites for each diagnostic outcome, namely, influenza A and its subtypes, influenza B, IgG & IgM for influenza A, and IgG & IgM for influenza B. The analytic cut-off values will be based on the pre-clinical study results. Performance metrics will be calculated as per CLSI guidance document I/LA18-A2, MM3-A2, and EP12-A2. outcomes will serve as the presumed truth. Each discrepant classification will be investigated and resolved (included by viral culture).

As described, a total of 900 subjects are planned to be enrolled in the prospective study. This sample size will provide sufficient subjects for the more common pathogens yielding low margins of error with a 95% confidence level for each performance metric. It is not anticipated that H5N1 and H7N9 strains will be encountered in the U.S. Furthermore, H1N1 seasonal strains were not common in recent respiratory infection seasons. Retrospective samples may be used to supplement the prospective study if insufficient samples are obtained for certain test outcomes. In general, if incidence rates are <3.5%, retrospectives and/or contrived samples will be included.

One of the objectives is to prepare regulatory submissions for Laboratory Developed Tests (LDTs) that were develop or have developed which operate on the SPU, LAS system.

Optionally, some embodiments may have a provision in the clinical study plan to collect nasal swabs and run them against the CDC RT-PCR method and method. Some known assays do not include intended use for nasal swabs (vs NPS).

Prospective samples of the H5N1 and H7N9 flu strains are difficult to acquire and it may be sufficient to conduct assay development and validation work on synthetic material and/or acquired purified genomic material.

While the Influenza ELISA assays are treated like quantitative assays and the results are antibody titers during the method characterization phase of development, the final nature of the assay is semi-quantitative (qualitative). Some embodiments may use quantitative versus qualitative Influenza ELISA assays for the intended use described herein.

APPENDIX

Representative Bench and Clinical Data
NAA Assay Validation Data:

The data presented below was collected during NAA assay development and validation and includes Limit of Detection (LOD), specificity, carry-over, inclusivity, exclusivity, precision and interference substances. The last part of this data section includes tests done on prospective clinical samples and compared with methods.

The Y-axis for each graph represents detection time in minutes. This data was further analyzed using a statistical model before a positive/negative value was assigned. Background information about this model is not included here but is described the "NAA Proposed Study Design(s), and Analytical and Pre-Clinical Performance—Determination of Assay Cutoffs" Section in accordance with the Draft Guidance for Industry and FDA Staff: "Medical Devices: The Pre-Submission Program and Meetings with FDA Staff." Each bar in the bar graphs below represents average values of at least eight replicates and variation is reflected by the error bars.

The data shown below is for the following assays:
Influenza A
Influenza subtype H1
Influenza subtype H1-2009
Influenza subtype H3
Influenza B
Influenza subtype H5N1
Influenza subtype H7
Influenza subtype N9
Representative NAA Study on Prospective Clinical Samples:

Clinical samples were tested with qPCR to confirm for the presence/absence of pathogen specific nucleic acid for various flu strains. These samples were then further tested with NAA and a subset of samples were tested with the relevant method, Biofire Filmarray RP. The below table shows the summary of results obtained, demonstrating a 100% concordance between qPCR, NAA and FilmarrayRP for the tested samples.

| | Representative Clinical sample study | | | | | |
| | qPCR confirmed sample | | NAA | | Biofire Filmarray RP | |
| Assay | Positive | Negative | Positive | Negative | Positive | Negative |
| --- | --- | --- | --- | --- | --- | --- |
| FluA H1N1 Pandemic | 8 | 15 | 8/8 | 15/15 | 2/2 | 3/3 |
| FluA H1N1 Seasonal | 7 | 11 | 7/7 | 11/11 | 2/2 | 2/2 |
| Flu A H1N1 Novel | 9 | 6 | 9/9 | 6/6 | 1/1 | 1/1 |
| Flu A H3N2 | 0 | 14 | 0/0 | 14/14 | 0/0 | 2/2 |
| Flu B | 6 | 24 | 6/6 | 24/24 | 2/2 | 3/3 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the although at least some embodiments are described in the context of SPUs located in locations physically remote from the central laboratory, some embodiments can also have one or more or all of the SPUs physically in the central laboratory. Optionally, some embodiments may have a combination of SPUs in the central laboratory and some SPUs located outside of the central laboratory. Although the term central laboratory is used in these examples, it should also be understood that for at least some embodiments herein, the laboratory in these examples need not be a central laboratory.

For some embodiments herein, as data is sent to the cloud, the metadata in the file may be corrupted or not provide desired information regarding when test was taken. Some embodiments herein may opt not to use any of the metadata associated with the data. Optionally, some embodiments may extract metadata at the device and include it as part of the data such as but not limited to a value of one or more the data fields that are transmitted, instead of residing in the background as metadata. Optionally, the harvesting of the metadata can occur in the cloud. It may continue to be part of the metadata of the file or it can be incorporated into one or more the data fields that are transmitted onward to the laboratory.

Some embodiments herein may include an opt-in and/or opt-out user interface page or question so that the user may select the privacy, clinical trial, and/or other participation in programs associated with the user and/or the test data.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc.
. . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are also fully incorporated herein by reference for all purposes: U.S. Patent Publication 2005/0100937, U.S. Pat. No. 8,380,541; U.S. Pat. App. Ser. No. 61/766,113, filed Feb. 18, 2013; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; U.S. Application Ser. No. 61/879,671 filed Sep. 18, 2013, U.S. Application Ser. No. 61/882,624 filed Sep. 25, 2013, and U.S. Application Ser. No. 61/673,245, filed Sep. 26, 2011, the disclosures of which patents and patent applications are all hereby incorporated by reference in their entireties. The following is also fully incorporated herein by reference for all purposes. Department of Health and Human Services, Letter providing Emergency Use Authorization (EUA) for emergency use of the CDC Human Influenza Virus Real-Time RT-PCR Diagnostic Panel-Influenza A/H7 Assay for detection of influenza A(H7N9) virus, Ranjna Chawla, PhD, Binita Goswami, MD, DNB, Devika Tayal, MD and V Mallika, MD, Identification of the Types of Preanalytical Errors in the Clinical Chemistry Laboratory: 1-Year Study at G. B. Pant Hospital. LabMedicine, 41, 89-92. 2010. http://labmed.ascpjournals.org/content/41/2/89.full.pdf&embedded=true; Lewin, The Value of Laboratory Screening and Diagnostic Tests for Prevention and Health Care Improvement 2009. http://www.lewin.com/~/media/Lewin/Site_Sections/Publications/Lewin%20Value%20LabTesting%20Sept%202009.pdf.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A method comprising:
   providing a sample processing unit comprising a liquid handling device comprising pipette assemblies, each of said pipette assemblies is independently actuatable in a vertical direction to access a sample,
   inserting a cartridge into the sample processing unit, the cartridge containing at least two types of reagents;
   picking up a magnet tool in the sample processing unit using a piston assembly in one of the pipette assemblies of the liquid handling device to interface with the magnet tool to pick up the magnet tool from a resting location in the sample processing unit outside of the pipette assemblies by extending a piston out of a nozzle of the one of the pipette assemblies to engage a proximal end of the magnet tool and retract the magnet tool back into the nozzle of the one of the pipette assemblies, wherein the proximal end engaged by the magnet tool is retractable upward into the nozzle and the magnet tool is extendable outward from the nozzle of the one of the pipette assemblies and detachable from the piston after use; and using one of the pipette assemblies of the sample processing unit to remove one or more of said reagents from the cartridge.

2. The method of claim 1, further comprising utilizing at least two types of pipette tips for transporting the sample or at least one or more of the reagents.

3. The method of claim 1, further comprising utilizing the liquid handling device to engage at least two contact points on a vessel in the cartridge to move the vessel from the cartridge to another location.

4. The method of claim 1, further comprising processing the sample by utilizing a centrifuge in the sample processing unit.

5. The method of claim 1, further comprising individually aspirating and dispensing fluids from each of said pipette assemblies.

6. The method of claim 1, further comprising imaging the sample by utilizing a luminometer in the sample processing unit.

7. The method of claim 1, further comprising imaging the sample by utilizing a fluorometer in the sample processing unit.

8. The method of claim 1, further comprising analyzing the sample by utilizing a spectrophotometer in the sample processing unit.

9. The method of claim 1, further comprising imaging the sample by performing microscopy in the sample processing unit.

10. The method of claim 1, further comprising processing the sample by utilizing a thermal control system comprising a plurality of temperature sensors and a plurality of heaters in the sample processing unit.

11. The method of claim 1 further comprising imaging the sample by utilizing a camera in the sample processing unit.

12. A method comprising:
providing a sample processing unit comprising a liquid handling device comprising pipette assemblies, each of said pipette assemblies is independently actuatable in a vertical direction to access a sample,
inserting a cartridge into the sample processing unit, the cartridge containing at least two types of reagents;
picking up a magnet tool in the sample processing unit using a piston assembly in one of the pipette assemblies of the liquid handling device to interface with the magnet tool to pick up the magnet tool from a resting location in the sample processing unit outside of the pipette assemblies by extending a piston out of a nozzle of the one of the pipette assemblies to engage a proximal end of the magnet tool and retract the magnet tool back into the nozzle of the one of the pipette assemblies, wherein the proximal end engaged by the magnet tool is retractable upward into the nozzle of the one of the pipette assemblies and the magnet tool is extendable outward from the nozzle and detachable from the piston after use;
using one of the pipette assemblies of the sample processing unit to remove one or more of said reagents from the cartridge; and
performing nucleic acid amplification on the sample in the sample processing unit.

13. A method comprising:
providing a sample processing unit comprising a liquid handling device comprising pipette assemblies, each of said pipette assemblies is independently actuatable in a vertical direction to access a sample,
inserting a cartridge into the sample processing unit, the cartridge containing at least two types of reagents;
picking up a magnet tool in the sample processing unit using a piston assembly in one of the pipette assemblies of the liquid handling device to interface with the magnet tool to pick up the magnet tool from a resting location in the sample processing unit outside of the pipette assemblies by extending a piston out of a nozzle of the one of the pipette assemblies to engage a proximal end of the magnet tool and retract the magnet tool back into the nozzle of the one of the pipette assemblies, wherein the proximal end engaged by the magnet tool is retractable upward into the nozzle of the one of the pipette assemblies and the magnet tool is extendable outward from the nozzle and detachable from the piston after use;
using one of the pipette assemblies of the sample processing unit to remove one or more of said reagents from the cartridge; and
sonicating the sample by utilizing a sonicator in the sample processing unit.

* * * * *